(12) United States Patent
Panicker

(10) Patent No.: US 10,556,893 B2
(45) Date of Patent: Feb. 11, 2020

(54) CYTOCHROME P450 INHIBITORS AND USES THEREOF

(71) Applicant: ANGION BIOMEDICA CORP., Uniondale, NY (US)

(72) Inventor: Bijoy Panicker, Holtsville, NY (US)

(73) Assignee: ANGION BIOMEDICA CORP., Uniondale, NY (US)

( * ) Notice: Subject to any disclaimer, the term of this patent is extended or adjusted under 35 U.S.C. 154(b) by 0 days.

(21) Appl. No.: 15/989,737

(22) Filed: May 25, 2018

(65) Prior Publication Data

US 2018/0334455 A1 Nov. 22, 2018

Related U.S. Application Data

(63) Continuation of application No. 15/503,267, filed as application No. PCT/US2015/044557 on Aug. 11, 2015, now Pat. No. 9,988,374.

(60) Provisional application No. 62/035,596, filed on Aug. 11, 2014.

(51) Int. Cl.

| C07D 417/06 | (2006.01) |
|---|---|
| A61K 31/428 | (2006.01) |
| A61P 3/10 | (2006.01) |
| A61P 35/00 | (2006.01) |
| A61P 1/16 | (2006.01) |

(52) U.S. Cl.
CPC .......... *C07D 417/06* (2013.01); *A61K 31/428* (2013.01); *A61P 1/16* (2018.01); *A61P 3/10* (2018.01); *A61P 35/00* (2018.01)

(58) Field of Classification Search
CPC .............................. C07D 417/06; A61K 31/428
See application file for complete search history.

(56) References Cited

U.S. PATENT DOCUMENTS

| 5,576,349 | A | 11/1996 | Leaf |
|---|---|---|---|
| 7,662,844 | B2 | 2/2010 | Smith et al. |
| 8,071,581 | B2 | 12/2011 | Smith et al. |
| 8,513,291 | B2 | 8/2013 | Panicker et al. |
| 8,865,752 | B2 | 10/2014 | Panicker et al. |
| 2006/0111408 | A1 | 5/2006 | Barlaam et al. |
| 2009/0054405 | A1 | 2/2009 | Booker et al. |

FOREIGN PATENT DOCUMENTS

| WO | WO1997049704 | 12/1997 |
|---|---|---|
| WO | WO2002003912 | 1/2002 |
| WO | WO2004067529 | 8/2004 |
| WO | WO2005000311 | 1/2005 |
| WO | WO2005007631 | 1/2005 |
| WO | WO2009153566 | 12/2009 |
| WO | WO2010036404 | 4/2010 |
| WO | WO2011082245 | 7/2011 |
| WO | WO2011153192 | 12/2011 |
| WO | WO2014/015137 | 1/2014 |
| WO | WO2014/093960 | 6/2014 |
| WO | WO2016109492 | 7/2016 |

OTHER PUBLICATIONS

Alizadeh et al., "Retinoids and Their Biological Effects Against Cancer", Int. Immunopharmacol., Jan. 2014; 18(1): 43-9.
Altucci et al., "The Promise of Retinoids to Fight Against Cancer", Nat. Rev. Cancer, Dec. 2001; 1(3): 181-93.
Nelson et al., "Therapeutic Potential of the Inhibition of the Retinoic Acid Hydroxylases CYP26A1 and CYP26B1 by Xenobiotics", Curr. Top. Med. Chem., Jun. 13, 2013; 13(12): 1402-28.
Labrie, "Blockade of Testicular and Adrenal Androgens in Prostate Cancer Treatment", Nat. Rev. Urol., Feb. 2011; 8(2): 73-85.
Roth et al., "Feasibility of Retinoids for the Treatment of Emphysema Study", Chest, Nov. 2006; 130(5): 1334-45.
Massaro et al., "Retinoic Acid Treatment Abrogates Elastase-Induced Pulmonary Emphysema in Rats", Nat. Med., Jun. 1997; 3(6): 675-7.
Massaro et al., "Retinoic Acid Treatment Partially Rescues Failed Septation in Rats and in Mice", Am. J. Physiol. Lung Cell Mol. Physiol., May 2000; 278(5): L955-L960.
Zhou et al., "All-Trans-Retinoic Acid Ameliorated High Fat Diet-Induced Atherosclerosis in Rabbits by Inhibiting Platelet Activation and Inflammation", J. Biomed. Biotechnol., 2012; 2012: 259693, PMCID:PMC3303861.
Wiegman et al., "All-Trans-Retinoic Acid Limits Restenosis After Balloon Angioplasty in the Focally Atherosclerotic Rabbit: A Favorable Effect on Vessel Remodeling", Arterioscler. Thromb. Vasc. Biol., Jan. 2000; 20(1): 89-95.
Claudel et al., "Reduction of Atherosclerosis in Apolipoprotein E Knockout Mice by Activation of the Retinoid X Receptor", Proc. Natl. Acad. Sci. U.S.A, Feb. 27, 2001; 98(5): 2610-5. PMCID:PMC30186.
Shudo et al., "Towards Retinoid Therapy for Alzheimer's Disease", Curr. Alzheimer. Res., Jun. 2009; 6(3): 302-11. PMCID:PMC2765081.
Goncalves et al., "Amyloid Beta Inhibits Retinoic Acid Synthesis Exacerbating Alzheimer Disease Pathology Which Can Be Attenuated by an Retinoic Acid Receptor Alpha Agonist", Eur. J. Neurosci., Apr. 2013; 37(7): 1182-92. PMCID:PMC3655538.
Lee et al., "All-Trans Retinoic Acid as a Novel Therapeutic Strategy for Alzheimer's Disease", Expert. Rev. Neurother., Nov. 2009; 9(11): 1615-21. PMCID:PMC2913310.

(Continued)

*Primary Examiner* — Karen Cheng
(74) *Attorney, Agent, or Firm* — Mark S. Cohen; Pearl Cohen Zedek Latzer Baratz LLP

(57) ABSTRACT

The present invention provides compounds having the general structural formula (I) (I) and pharmaceutically acceptable derivatives thereof, as described generally and in classes and subclasses herein, and additionally provides pharmaceutical compositions thereof, and methods for the use thereof for the treatment of any of a number of conditions or diseases involving fibrosis and proliferation, and where anti-fibrotic or anti-proliferative activity is beneficial.

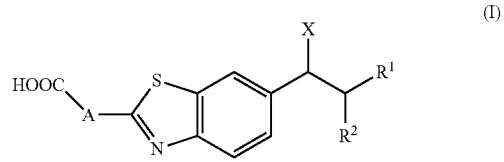

(I)

21 Claims, No Drawings

(56) References Cited

OTHER PUBLICATIONS

Rao et al., "All-Trans Retinoic Acid Alleviates Hepatic Ischemia/Reperfusion Injury by Enhancing Manganese Superoxide Dismutase in Rats", Biol. Pharm. Bull., 2010; 33(5): 869-75.

Rao et al., "All-Trans Retinoic Acid Preconditioning Protects Against Liver Ischemia/Reperfusion Injury by Inhibiting the Nuclear Factor Kappa B Signaling Pathway", J. Surg. Res., Apr. 2013; 180(2): e99-e106.

Harvey et al., "Midkine and Retinoic Acid Reduce Cerebral Infarction Induced by Middle Cerebral Artery Ligation in Rats", Neurosci. Lett., Oct. 14, 2004; 369(2): 138-41.

Li et al., "The Effects of Retinoic Acid on the Expression of Neurogranin After Experimental Cerebral Ischemia", Brain Res., Aug. 21, 2008; 1226: 234-40.

Perez et al., "Beneficial Effect of Retinoic Acid on the Outcome of Experimental Acute Renal Failure", Nephrol. Dial. Transplant., Oct. 2004; 19(10): 2464-71.

Shen et al., "9-Cis-Retinoic Acid Reduces Ischemic Brain Injury in Rodents Via Bone Morphogenetic Protein", J. Neurosci. Res., Feb. 2009; 87(2): 545-55. PMCID:PMC2628966.

Wang et al., "Chronic Alcohol Intake Reduces Retinoic Acid Concentration and Enhances AP-1 (c-Jun and c-Fos) Expression in Rat Liver", Hepatology, Sep. 1998; 28(3): 744-50.

Wang et al., "Chronic Alcohol Intake Interferes with Retinoid Metabolism and Signaling", Nutr. Rev., Feb. 1999; 57(2): 51-9.

Kim et al., "All-Trans-Retinoic Acid Ameliorates Hepatic Steatosis in Mice by a Novel Transcriptional Cascade", Hepatology, May 2014; 59(5): 1750-60. PMCID:PMC4008145.

He et al., "Combination of Retinoic Acid and Ursodeoxycholic Acid Attenuates Liver Injury in Bile Duct-Ligated Rats and Human Hepatic Cells", Hepatology, Feb. 2011; 53(2): 548-57. PMCID:PMC3069505.

Abdelmalek et al., "Retinoids and Wound Healing", Dermatol. Surg., Oct. 2006; 32(10): 1219-30.

Jiang et al., "Effect of ATRA on Contents of Liver Retinoids, Oxidative Stress and Hepatic Injury in Rat Model of Extrahepatic Cholestasis", J. Huazhong. Univ. Sci. Technolog. Med. Sci., Oct. 2007; 27(5): 491-4.

Yoshikawa et al., "A Retinoic Acid Receptor Agonist Tamibarotene Suppresses Iron Accumulation in the Liver", Obesity,(Silver.Spring) Jan. 2013; 21(1): E22-E25.

Kim et al., "All-Trans-Retinoic Acid Rescues Neurons After Global Ischemia by Attenuating Neuroinflammatory Reactions", Neurochem. Res., Dec. 2013; 38(12): 2604-15.

Petersen et al., "Alitretinoin—Its Use in Intractable Hand Eczema and Other Potential Indications", Drug Design, Development and Therapy, 2009; 3: 51-7.

DiGiovanna et al., "Systemic Retinoids in the Management of Ichthyoses and Related Skin Types" Dermatol. Ther., 2013; 26(1).

Mukherjee et al., "Retinoids in the Treatment of Skin Aging: An Overview of Clinical Efficacy and Safety", Clinical Interventions in Aging, 2006: 1(4): 327-48.

Kwok et. al., "Retinoic Acid Attenuates Rheumatoid Inflammation in Mice", J. Immnol., 2012; 189: 1062-71.

Bilbija et al., "Retinoic Acid Signalling is Activated in the Postischemic Heart and May Influence Remodelling", PLoS.ONE., 2012; 7(9): e44740. PMCID:PMC3460971.

Xiao et al., "Retinoic Acids Exhibit Anti-Fibrotic Activity Through the Inhibition of 5-Lipoxygenase Expression in Scleroderma Fibroblasts", J. Dermatol., Apr. 2011; 38(4): 345-53.

Ozdemir et al., "Treatment of Plaque-Type Localized Scleroderma with Retinoic Acid and Ultraviolet a Plus the Photosensitizer Psoralen: A Case Series", J. Eur. Acad. Dermatol. Venereol., Apr. 2008; 22(4): 519-21.

Delany et al., "The Synthetic Retinoid (4-hydroxyphenyl)retinamide Decreases Collagen Expression in vitro and in the Tight-Skin Mouse", Arthritis Rheum., Jul. 1993; 36(7): 983-93.

Kolarcik et al., "Retinoid Signaling Alterations in Amyotrophic Lateral Sclerosis", Am. J. Neurodegener. Dis., 2012; 1(2): 130-45. PMCID:PMC3560459.

Krueger et al., "Identification of Retinoic Acid in a High Content Screen for Agents that Overcome the Anti-Myogenic Effect of TGF-beta-1. PLoS.ONE", 2010; 5(11): e15511. PMCID:PMC2994897.

Yin et al., "Early Post-Treatment with 9-cis Retinoic Acid Reduces Neurodegeneration of Dopaminergic Neurons in a Rat Model of Parkinson's Disease", BMC. Neurosci, 2012; 13: 120. PMCID:PMC3523975.

Geria et al., "Talarozole, A Selective Inhibitor of P450-Mediated All-Trans Retinoic Acid for the Treatment of Psoriasis and Acne", Curr. Opin. Investig. Drugs, Nov. 2008; 9(11): 1228-37.

Njar et al., "Retinoic Acid Metabolism Blocking Agents (RAMBAs) for Treatment of Cancer and Dermatological Diseases", Bioorg. Med. Chem., Jul. 1, 2006; 14(13): 4323-40.

Zhang et al., "Cell Cycle Genes as Targets of Retinoid Induced Ovarian Tumor Cell Growth Suppression", Oncogene Nov. 29, 2001; 20(55): 7935-44.

Pan et al., "CoMFA and Molecular Docking Studies of Benzoxazomes and Benzothiazoles as CYP450 1A1 Inhibitors", European Journal of Medicinal Chemistry, 2010; 45: 967-97.

Bradshaw et al., "The Development of the Anti-Tumor Benzothiazole Prodrug, Phortress, as a Clinical Candidate", Curr. Med. Chem., 2004; 11: 1009-21.

Nativelle-Serpentini et al., "Synthesis and Evaluation of Benzoxazolinonic Imidazoles and Derivatives as Non-Steroidal Aromatase Inhibitors", J. Enz. Inhib. 2004; 19: 119-127.

International Search Report, WO2011/153192 (PCT/US2011/038695) Published Apr. 19, 2012.

Japanese Office Action, dated Apr. 12, 2019, from corresponding Japanese Patent Application No. 2017-507721.

Chinese Office Action, dated Jun. 5, 2019, from corresponding Chinese Patent Application No. 201580048388.5.

CYTOCHROME P450 INHIBITORS AND USES THEREOF

CROSS-REFERENCE TO RELATED APPLICATIONS

This application is a continuation of U.S. patent application Ser. No. 15/503,267, filed Feb. 10, 2017, now U.S. Pat. No. 9,988,374, which is a National Phase Application of PCT International Application No. PCT/US2015/044557, filed Aug. 11, 2015, which claims priority from U.S. Provisional Application No. 62/035,596, filed Aug. 11, 2014, which are hereby incorporated by reference.

GOVERMENT SUPPORT

This invention was made with government support under NS045373 awarded by the National Institutes of Health. The government has certain right in the invention.

BACKGROUND OF THE INVENTION

Numerous diseases and conditions responsible for significant morbidity as well as mortality have as an underlying disease mechanism the inappropriate or excessive production of fibrous connective tissue, a process generally known as fibrosis. Such diseases and conditions include by way of non-limiting examples, fibrotic liver disease, cirrhosis, cardiac fibrosis and lung fibrosis including idiopathic pulmonary fibrosis. In addition to these, numerous other conditions and diseases exhibit a fibrotic component, including but not limited to hepatic ischemia-reperfusion injury, cerebral infarction, chronic obstructive pulmonary diseases including emphysema, pancreatic fibrosis, ischemic heart disease, heart failure and renal disease including renal fibrosis. These conditions and diseases exact a major toll on the healths of afflicted individuals, and on the health care system. Other conditions such as the skin condition ichthyosis, and photodamage and aging of the skin, and other changes to the appearance of the skin also exact a toll to health and well being of afflicted individuals. Wrinkling including crow's feet are of particular concern to many individuals.

Furthermore, dysproliferative diseases including cancer are also major diseases with significant impact to the patients as well as the health care system.

Means to affect the onset or progression of such conditions and diseases would be highly desirable.

SUMMARY OF THE INVENTION

In one embodiment, compounds are provided that are useful for, among other purposes, the prevention, treatment or lessening of the severity of a condition or disease associated with or characterized by increased, excessive or inappropriate fibrosis, or characterized by cellular dysproliferation, represented by Formula (I):

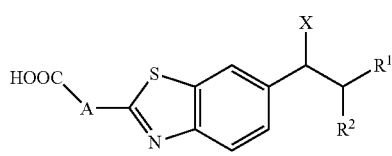

(I)

or an E or Z isomer thereof, syn or anti isomer thereof, an optically pure isomer thereof, or pharmaceutically acceptable salt thereof, wherein:

X is a triazole, which is optionally substituted with one or more independent $R^5$ substituents;

$R^1$ and $R^2$ are each independently hydrogen or lower alkyl;

A is

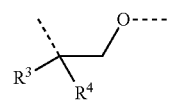

or an aryl, either of which is optionally substituted with one or more independent $R^5$ substituents;

$R^3$ and $R^4$ are each independently hydrogen or a lower alkyl which is optionally substituted with one or more $R^5$ substituents; or $R^3$ with $R^4$, taken together with the carbon atom to which they are attached, form a carbonyl or 3-10 membered saturated or unsaturated monocyclic or polycyclic ring, wherein said ring is optionally substituted with one or more $R^5$;

each occurrence of $R^5$ is independently hydrogen, halogen, cyano, hydroxy, nitro, $-SO_2NR^6R^7$, $-CONR^6R^7$ or $-NR^6R^7$, haloalkyl, or a lower alkyl group; and $R^6$ and $R^7$ are each independently hydrogen or a lower alkyl group.

In another embodiment, pharmaceutical compositions comprising a compound of Formula (I) and a pharmaceutically acceptable carrier, excipient or diluent, are embraced herein.

In another embodiment, each occurrence of $R^5$ is independently hydrogen, halogen, cyano, hydroxy, nitro or a lower alkyl group.

In further embodiment, a compound is represented by Formula (I), or an E or Z isomer thereof, syn or anti isomer thereof, an optically pure isomer thereof, or pharmaceutically acceptable salt thereof, wherein A is aryl, and the other variables are as described above. In one embodiment, when A is aryl, $R^1$ and $R^2$ are each independently hydrogen or lower alkyl. In one embodiment, when A is aryl, $R^1$ and $R^2$ are each lower alkyl. In one embodiment, when A is unsubstituted aryl, $R^1$ and $R^2$ are each lower alkyl. In one embodiment, when A is substituted aryl, $R^1$ and $R^2$ are each lower alkyl.

In further embodiment, compounds useful for the purposes described herein are represented by Formula (II):

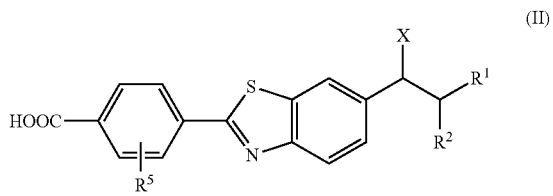

(II)

or an E or Z isomer thereof, syn or anti isomer thereof, an optically pure isomer thereof, or pharmaceutically acceptable salt thereof, and wherein all other substituents are as defined herein above.

In one embodiment, when A is aryl, $R^1$ and $R^2$ are each independently hydrogen or lower alkyl. In one embodiment, when A is aryl, $R^1$ and $R^2$ are each lower alkyl. In one embodiment, when A is unsubstituted aryl, $R^1$ and $R^2$ are each lower alkyl. In one embodiment, when A is substituted aryl, $R^1$ and $R^2$ are each lower alkyl.

In another embodiment, each occurrence of $R^5$ is independently hydrogen, halogen, cyano, hydroxy, nitro, $-SO_2NR^6R^7$, $-CONR^6R^7$ or $-NR^6R^7$, haloalkyl, or a lower alkyl group. In another embodiment, each occurrence of $R^5$ is independently hydrogen, halogen, cyano, hydroxy, nitro or a lower alkyl group.

In another embodiment, a compound is represented by Formula (I), or an E or Z isomer thereof, syn or anti isomer thereof, an optically pure isomer thereof, or pharmaceutically acceptable salt thereof, wherein A is

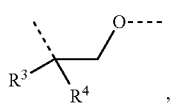

and the other variables are as described above.

In another embodiment, compounds useful for the purposes described herein are represented by Formula (III):

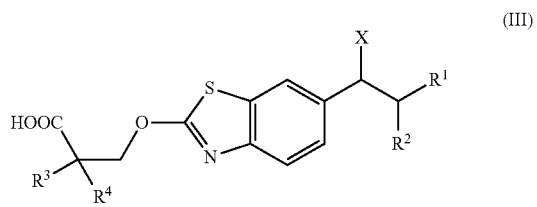

(III)

or an E or Z isomer thereof, syn or anti isomer thereof, an optically pure isomer thereof, or pharmaceutically acceptable salt thereof, and wherein all substituents are as defined herein above In another embodiment, each occurrence of $R^5$ is independently hydrogen, halogen, cyano, hydroxy, nitro or a lower alkyl group.

In another embodiment, the invention provides compositions including pharmaceutical compositions of any of the compounds of Formulae (I)-(III) disclosed herein. Such pharmaceutical compositions can comprise a carrier, excipient or diluent.

In another embodiment, the aforementioned formulae, compounds and pharmaceutical compositions have anti-fibrotic activities and thus are useful for the prevention, treatment or lessening of the severity of a condition or disease associated with or characterized by increased, excessive or inappropriate fibrosis. In another embodiment, the aforementioned formulae, compounds and pharmaceutical formulations have anti-dysproliferative activities and thus are useful for the prevention, treatment or lessening of the severity of a condition or disease associated with or characterized by increased, excessive or inappropriate proliferation, such as cancer.

In another aspect, the invention provides methods for the use of any of the compounds disclosed herein for treating or lessening the severity of a disease or condition associated with inappropriate fibrosis. In certain embodiments, the method is for treating or lessening the severity of a disease or condition selected from fibrotic liver disease, cirrhosis, cardiac fibrosis and lung fibrosis including idiopathic pulmonary fibrosis; hepatic ischemia-reperfusion injury, cerebral infarction, chronic obstructive pulmonary diseases including emphysema, pancreatic fibrosis, ischemic heart disease, heart failure and renal disease including renal fibrosis, fibrotic liver disease, hepatic ischemia-reperfusion injury, cerebral infarction, ischemic heart disease, and renal disease or lung (pulmonary) fibrosis. In certain embodiments, the method is for treating or lessening the severity of a disease or condition selected from liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke; cerebrovascular disease; myocardial ischemia; atherosclerosis; renal failure; renal fibrosis or idiopathic pulmonary fibrosis. In certain exemplary embodiments, the method is for the treatment of wounds for acceleration of healing; vascularization of a damaged and/or ischemic organ, transplant or graft; amelioration of ischemia/reperfusion injury in the brain, heart, liver, kidney, and other tissues and organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; amyotrophic lateral sclerosis, muscular dystrophy, scleroderma, chronic obstructive pulmonary disease, emphysema, diabetes mellitus, multiple sclerosis, trauma to the central nervous system, and hereditary neurodegenerative disorders including the leukodystrophies such as metachromatic leukodystrophy, Refsum's disease, adrenoleukodystrophy, Krabbe's disease, phenylketonuria, Canavan disease, Pelizaeus-Merzbacher disease and Alexander's disease.

In addition, compounds of the invention are useful in the treatment of dysproliferative diseases including cancer, psoriasis, rheumatoid arthritis, and other inflammatory joint and skin diseases. In one embodiment, the compounds are useful in the treatment of prostate cancer. In one embodiment, the compounds are useful in the treatment of breast cancer. In one embodiment the compounds are useful in the treatment of ovarian cancer.

In another embodiment, compounds of the invention are useful for prevention and treatment of other cancerous and precancerous conditions, including, for example, premalignant and malignant hyperproliferative diseases such as cancers of the breast, skin, prostate, colon, bladder, cervix, uterus, stomach, lung, esophagus, blood and lymphatic system, larynx, oral cavity, metaplasias, dysplasias, neoplasias, leukoplakias and papillomas of the mucous membranes, and in the treatment of Kaposi's sarcoma. In addition, inventive compounds can also be used as agents to treat diseases of the eye, including, for example, proliferative vitreoretinopathy, retinal detachment, corneopathies such as dry eye, as well as in the treatment and prevention of various cardiovascular diseases, including, without limitation, diseases associated with lipid metabolism such as dyslipidemias, prevention of post-angioplasty restenosis and as an agent to increase the level of circulation tissue plasminogen activator. Other uses include the prevention and treatment of conditions and diseases associated with human papilloma virus (HPV), including warts, various inflammatory diseases such as pulmonary fibrosis, ileitis, colitis and Crohn's disease, neurodegenerative diseases such as Alzheimer's disease, Parkinson's disease and stroke, improper pituitary function, including insufficient production of growth hormone, modulation of apoptosis, including both the induction of apoptosis, restoration of hair growth, including combination therapies with the present compounds and other agents such as minoxidil, diseases associated with the immune systems, including use of the present compounds as immunosuppressant and immunostimulants, modulation of organ transplant rejection and facilitation of wound healing, including modulation of chelosis. Compounds are also useful in treating type II non-insulin dependent diabetes mellitus (NIDDM).

The present invention is also directed to treatment of non-malignant tumors and other disorders involving inappropriate cell or tissue growth by administering a therapeutically effective amount of an agent of the invention. For example, it is contemplated that the invention is useful for the treatment of arteriovenous (AV) malformations, particularly in intracranial sites. The invention may also be used to treat psoriasis, a dermatologic condition that is characterized by inflammation and vascular proliferation; benign prostatic hypertrophy, a condition associated with inflammation and possibly vascular proliferation; and cutaneous fungal infections. Treatment of other hyperproliferative disorders is also contemplated. The agents may also be used topically to remove warts, birthmarks, moles, nevi, skin tags, lipomas, angiomas including hemangiomas, and other cutaneous lesions for cosmetic or other purposes.

Furthermore, compounds of the invention are also useful for the treatment of various skin diseases, such as actinic keratoses, arsenic keratoses, inflammatory and non-inflammatory acne, psoriasis, ichthyoses, keratinization and hyperproliferative disorders of the skin, eczema, atopic dermatitis, Darriers disease and lichen planus; for preventing, treating, and reversal of glucocorticoid, age, and photo damage to the skin. Such damage can manifest as lines and wrinkling of the face and other parts of the body, including crow's feet, which are of particular concern to many individuals. Ichthyoses includes various forms of ichthyosis, such as but not limited to ichthyosis vulgaris, lamellar ichthyosis, X-linked ichthyosis, congenital ichthyosiform erythroderma, epidermolytic hyperkeratosis (bullous ichthyosis), harlequin-type ichthyosis, ichthyosis bullosa of Siemens, ichthyosis hystrix, Curth-Macklin type, hystrix-like ichthyosis with deafness, lamellar ichthyosis, type 1, lamellar ichthyosis, type 2, lamellar ichthyosis, type 3 lamellar ichthyosis, type 4, lamellar ichthyosis, type 5, and autosomal recessive congenital ichthyosis.

Furthermore, the compounds embodied herein inhibit the activity of cytochrome P450 (CYP) enzyme CYP26. Although disclosure of the mechanism by which embodiments herein operate is not required nor are Applicants bound thereto, inhibitors of CYP26 increase the levels of all-trans retinoic acid (ATRA), which increase is beneficial in various conditions and diseases as described herein, such as but not limited to the fibrotic process and dysproliferative diseases. In one embodiment, compounds embodied herein show selectivity at inhibiting CYP26 as compared to other CYP enzymes.

In another embodiment, compounds of the invention as well as compositions and formulations thereof are therapeutically beneficial when administered at a time after the onset of the acute disease or acute condition or time of injury. In certain instances administration at least 3 hours after onset is beneficial. In other embodiments administration at least 24 hours after onset is beneficial. In certain other embodiments administration at least 1-3 weeks after onset is beneficial. In other embodiments methods are provided for treating an acute disease or condition wherein compound is administered at a time after the onset or induction of the disease or condition. In other embodiments, temporal separation of the induction, onset, recurrence or recrudescence of a disease or injury, and the optimal effective response to an antifibrotic or antidysproliferative compound, provides guidance to the timing of administration of a compound of the invention or a composition of formulation thereof. In other embodiments, a disease, condition or injury can be prevented by prophylactic administration of a compound embodied herein prior to the injury, exposure, or other anticipated sustaining of pathology.

Definitions

Unless otherwise stated, the connections of compound name moieties are at the rightmost recited moiety. That is, the substituent name starts with a terminal moiety, continues with any bridging moieties, and ends with the connecting moiety. For example, hetarylthio$C_{1-4}$alkyl has a heteroaryl group connected through a thio sulfur to a $C_{1-4}$ alkyl that connects to the chemical species bearing the substituent.

As used herein, for example, "lower alky;" or "lower-alkyl" is used to mean an alkyl having 0-6 carbons—that is, 0, 1, 2, 3, 4, 5 or 6 carbons in a straight or branched configuration. An alkyl having no carbon is hydrogen when the alkyl is a terminal group. An alkyl having no carbon is a direct bond when the alkyl is a bridging (connecting) group.

In all embodiments of this invention, the term "alkyl" includes both branched and straight chain alkyl groups. Typical alkyl groups are methyl, ethyl, n-propyl, isopropyl (iPr), n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl and the like.

The term "halo" or "halogen" refers to fluoro, chloro, bromo or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl and the like.

The term "cycloalkyl" or "saturated ring" or "monocyclic ring" refer to a cyclic aliphatic ring structure, optionally substituted with alkyl, hydroxy and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl and the like.

The term "bicycloalkyl" refers to two cycloalkyl rings fused together and the term "bridged bicycloalkyl" refers to two rings joined together forming a bridged structure, for example bicyclo[3.2.1]octane, bicyclo[2.2.1]heptane, bicyclo[2.2.2]octane and the like. The term "polycyclic" refers to two or more cycloalkyl rings fused together, for example bicyclo[3.1.0]hexane and octahydropentalene and the like.

The term "alkylcarbonyloxyalkyl" refers to an ester moiety, for example acetoxymethyl, n-butyryloxyethyl and the like.

The term "alkynylcarbonyl" refers to an alkynylketo functionality, for example propynoyl and the like.

The term "hydroxyalkyl" refers to an alkyl group substituted with one or more hydroxy groups, for example hydroxymethyl, 2,3-dihydroxybutyl and the like.

The term "alkylsulfonylalkyl" refers to an alkyl group substituted with an alkylsulfonyl moiety, for example mesylmethyl, isopropylsulfonylethyl and the like.

The term "alkylsulfonyl" refers to a sulfonyl moiety substituted with an alkyl group, for example mesyl, n-propylsulfonyl and the like.

The term "acetylaminoalkyl" refers to an alkyl group substituted with an amide moiety, for example acetylaminomethyl and the like.

The term "acetylaminoalkenyl" refers to an alkenyl group substituted with an amide moiety, for example 2-(acetylamino)vinyl and the like.

The term "alkenyl" refers to an ethylenically unsaturated hydrocarbon group, straight or branched chain, having 1 or 2 ethylenic bonds, for example vinyl, allyl, 1-butenyl, 2-butenyl, isopropenyl, 2-pentenyl and the like.

The term "haloalkenyl" refers to an alkenyl group substituted with one or more halo groups.

The term "unsaturated ring" refers to a substituted or unsubstituted "cycloalkenyl" or a phenyl group.

The term "cycloalkenyl" refers to a cyclic aliphatic ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl and the like.

The term "alkynyl" refers to an unsaturated hydrocarbon group, straight or branched, having 1 or 2 acetylenic bonds, for example ethynyl, propargyl and the like.

The term "haloalkynyl" refers to an alkynyl group substituted with one or more halo groups.

The term "alkylcarbonyl" refers to an alkylketo functionality, for example acetyl, n-butyryl and the like.

The term "alkenylcarbonyl" refers to an alkenylketo functionality, for example, propenoyl and the like.

The term "aryl" refers to phenyl or naphthyl which may be optionally substituted. Typical aryl groups include, but are not limited to, phenyl, 4-chlorophenyl, 4-fluorophenyl, 4-bromophenyl, 3-chlorophenyl, 3-fluorophenyl, 3-nitrophenyl, 3-(trifluoromethyl)phenyl, 2-methoxyphenyl, 2-methylphenyl, 3-methyphenyl, 4-methylphenyl, 4-ethylphenyl, 2-methyl-3methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl and 2-iodo-4-methylphenyl.

The term "heterocyclic unsaturated ring" refers to a substituted or unsubstituted "heteroaryl" or a heteroaliphatic ring structure having 1 or 2 ethylenic bonds such as dihydropyridine, tetrahydropyridine, dihydropyrrole, dihydroimidazole and the like.

The terms "heteroaryl" or "hetaryl" refer to a substituted or unsubstituted 3-10 membered unsaturated ring containing one, two, three or four heteroatoms, preferably one or two heteroatoms independently selected from oxygen, nitrogen and sulfur or to a bicyclic unsaturated ring system containing up to 10 atoms including at least one heteroatom selected from oxygen, nitrogen and sulfur. Examples of heteroaryls include, but are not limited to, 2-pyridinyl (synonym: 2-pyridyl), 3-pyridinyl (synonym: 3-pyridyl) or 4-pyridinyl (synonym: 4-pyridyl), pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, and benzothienyl. The heterocyclic ring may be optionally substituted with up to two substituents.

The terms "aryl-alkyl" or "arylalkyl" are used to describe a group wherein the alkyl chain can be branched or straight chain with the aryl portion, as defined hereinbefore, forming a bridging portion of the aryl-alkyl moiety. Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl)butyl, 4-(2,4-dichlorophenyl)butyl, 4-(2-methoxyphenyl)butyl and 10-phenyldecyl.

The terms "aryl-cycloalkyl" or "arylcycloalkyl" are used to describe a group wherein the aryl group is attached to a cycloalkyl group, for example phenylcyclopentyl and the like.

The terms "aryl-alkenyl" or "arylalkenyl" are used to describe a group wherein the alkenyl chain can be branched or straight chain with the aryl portion, as defined hereinbefore, forming a bridging portion of the aralkenyl moiety, for example styryl (2-phenylvinyl), phenpropenyl and the like.

The terms "aryl-alkynyl" or "arylalkynyl" are used to describe a group wherein the alkynyl chain can be branched or straight chain with the aryl portion, as defined hereinbefore, forming a bridging portion of the aryl-alkynyl moiety, for example 3-phenyl-1-propynyl and the like.

The terms "aryl-oxy" or "aryloxy" are used to describe a terminal aryl group attached to a bridging oxygen atom. Typical aryl-oxy groups include phenoxy, 3,4-dichlorophenoxy and the like.

The terms "aryl-oxyalkyl" or "aryloxyalkyl" are used to describe a group wherein an alkyl group is substituted with an aryl-oxy group, for example pentafluorophenoxymethyl and the like.

The terms "hetaryl-oxy" or "heteroaryl-oxy" or "hetaryloxy" or "heteroaryloxy" are used to describe a terminal hetaryl group attached to a bridging oxygen atom. Typical hetaryl-oxy groups include 4,6-dimethoxypyrimidin-2-yloxy and the like.

The terms "hetarylalkyl" or "heteroarylalkyl" or "hetaryl-alkyl" or "heteroaryl-alkyl" are used to describe a group wherein the alkyl chain can be branched or straight chain with the heteroaryl portion, as defined hereinbefore, forming a bridging portion of the heteroaralkyl moiety, for example 3-furylmethyl, thienyl, furfuryl and the like.

The terms "hetarylalkenyl" or "heteroarylalkenyl" or "hetaryl-alkenyl" or "heteroaryl-alkenyl" are used to describe a group wherein the alkenyl chain can be branched or straight chain with the heteroaryl portion, as defined hereinbefore, forming a bridging portion of the heteroaralkenyl moiety, for example 3-(4-pyridyl)-1-propenyl.

The terms "hetarylalkynyl" or "heteroarylalkynyl" or "hetaryl-alkynyl" or "heteroaryl-alkynyl" are used to describe a group wherein the alkynyl chain can be branched or straight chain with the heteroaryl portion, as defined hereinbefore, forming a bridging portion of the heteroaralkynyl moiety, for example 4-(2-thienyl)-1-butynyl.

The term "heterocyclyl" or "heterocyclic saturated ring" refers to a substituted or unsubstituted 3-10 membered saturated ring containing one, two or three heteroatoms, preferably one or two heteroatoms independently selected from oxygen, nitrogen and sulfur or to a bicyclic ring system containing up to 10 atoms including at least one heteroatom selected from oxygen, nitrogen and sulfur wherein the ring containing the heteroatom is saturated. Examples of heterocyclyls include, but are not limited to, tetrahydrofuranyl, tetrahydrofuryl, pyrrolidinyl, piperidinyl, 4-pyranyl, tetrahydropyranyl, thiolanyl, morpholinyl, piperazinyl, dioxolanyl, dioxanyl, indolinyl and 5-methyl-6-chromanyl.

The term "monoheterocyclic" refers to a single heterocyclic ring structure, while "polyheterocyclic" refers to more than one ring fused together to form a heterocyclic structure.

The terms "heterocyclylalkyl" or "heterocyclyl-alkyl" are used to describe a group wherein the alkyl chain can be branched or straight chain with the heterocyclyl portion, as defined hereinabove, forming a bridging portion of the heterocyclylalkyl moiety, for example 3-piperidinylmethyl and the like.

The terms "heterocyclylalkenyl" or "heterocyclyl-alkenyl" are used to describe a group wherein the alkenyl chain can be branched or straight chain with the heterocyclyl portion, as defined hereinbefore, forming a bridging portion of the heterocyclylalkenyl moiety, for example 2-morpholinyl-1-propenyl.

The terms "heterocyclylalkynyl" or "heterocyclyl-alkynyl" are used to describe a group wherein the alkynyl chain can be branched or straight chain with the heterocyclyl portion, as defined hereinbefore, forming a bridging portion of the heterocyclylalkynyl moiety, for example 2-pyrrolidinyl-1-butynyl.

The term "carboxylalkyl" includes both branched and straight chain alkyl groups as defined hereinbefore attached to a carboxyl (—COOH) group.

The term "carboxylalkenyl" includes both branched and straight chain alkenyl groups as defined hereinbefore attached to a carboxyl (—COOH) group.

The term "carboxylalkynyl" includes both branched and straight chain alkynyl groups as defined hereinbefore attached to a carboxyl (—COOH) group.

The term "carboxylcycloalkyl" refers to a carboxyl (—COOH) group attached to a cyclic aliphatic ring structure as defined hereinbefore.

The term "carboxylcycloalkenyl" refers to a carboxyl (—COOH) group attached to a cyclic aliphatic ring structure having 1 or 2 ethylenic bonds as defined hereinbefore.

The terms "cycloalkylalkyl" or "cycloalkyl-alkyl" refer to a cycloalkyl group as defined hereinbefore attached to an alkyl group, for example cyclopropylmethyl, cyclohexylethyl and the like.

The terms "cycloalkylalkenyl" or "cycloalkyl-alkenyl" refer to a cycloalkyl group as defined hereinbefore attached to an alkenyl group, for example cyclohexylvinyl, cycloheptylallyl and the like.

The terms "cycloalkylalkynyl" or "cycloalkyl-alkynyl" refer to a cycloalkyl group as defined hereinbefore attached to an alkynyl group, for example cyclopropylpropargyl, 4-cyclopentyl-2-butynyl and the like.

The terms "cycloalkenylalkyl" or "cycloalkenyl-alkyl" refer to a cycloalkenyl group as defined hereinbefore attached to an alkyl group, for example 2(cyclopenten-1-yl) ethyl and the like.

The terms "cycloalkenylalkenyl" or "cycloalkenyl-alkenyl" refer to a cycloalkenyl group as defined hereinbefore attached to an alkenyl group, for example 1-(cyclohexen-3-yl)allyl and the like.

The terms "cycloalkenylalkynyl" or "cycloalkenyl-alkynyl" refer to a cycloalkenyl group as defined hereinbefore attached to an alkynyl group, for example 1-(cyclohexen-3-yl)propargyl and the like.

The term "carboxylcycloalkylalkyl" refers to a carboxyl (—COOH) group attached to the cycloalkyl ring portion of a cycloalkylalkyl group as defined hereinbefore.

The term "carboxylcycloalkylalkenyl" refers to a carboxyl (—COOH) group attached to the cycloalkyl ring portion of a cycloalkylalkenyl group as defined hereinbefore.

The term "carboxylcycloalkylalkynyl" refers to a carboxyl (—COOH) group attached to the cycloalkyl ring portion of a cycloalkylalkynyl group as defined hereinbefore.

The term "carboxylcycloalkenylalkyl" refers to a carboxyl (—COOH) group attached to the cycloalkenyl ring portion of a cycloalkenylalkyl group as defined hereinbefore.

The term "carboxylcycloalkenylalkenyl" refers to a carboxyl (—COOH) group attached to the cycloalkenyl ring portion of a cycloalkenylalkenyl group as defined hereinbefore.

The term "carboxylcycloalkenylalkynyl" refers to a carboxyl (—COOH) group attached to the cycloalkenyl ring portion of a cycloalkenylalkynyl group as defined hereinbefore.

The term "alkoxy" includes both branched and straight chain terminal alkyl groups attached to a bridging oxygen atom. Typical alkoxy groups include methoxy, ethoxy, n-propoxy, isopropoxy, tert-butoxy and the like.

The term "haloalkoxy" refers to an alkoxy group substituted with one or more halo groups, for example chloromethoxy, trifluoromethoxy, difluoromethoxy, perfluoroisobutoxy and the like.

The term "alkoxyalkoxyalkyl" refers to an alkyl group substituted with an alkoxy moiety which is in turn substituted with a second alkoxy moiety, for example methoxymethoxymethyl, isopropoxymethoxyethyl and the like.

The term "alkylthio" includes both branched and straight chain alkyl groups attached to a bridging sulfur atom, for example methylthio.

The term "haloalkylthio" refers to an alkylthio group substituted with one or more halo groups, for example trifluoromethylthio.

The term "alkoxyalkyl" refers to an alkyl group substituted with an alkoxy group, for example isopropoxymethyl.

The term "alkoxyalkenyl" refers to an alkenyl group substituted with an alkoxy group, for example 3-methoxyallyl.

The term "alkoxyalkynyl" refers to an alkynyl group substituted with an alkoxy group, for example 3-methoxypropargyl.

The term "alkoxycarbonylalkyl" refers to a straight chain or branched alkyl substituted with an alkoxycarbonyl, for example ethoxycarbonylmethyl, 2-(methoxycarbonyl)propyl and the like.

The term "alkoxycarbonylalkenyl" refers to a straight chain or branched alkenyl as defined hereinbefore substituted with an alkoxycarbonyl, for example 4-(ethoxycarbonyl)-2-butenyl and the like.

The term "alkoxycarbonylalkynyl" refers to a straight chain or branched alkynyl as defined hereinbefore substituted with an alkoxycarbonyl, for example 4-(ethoxycarbonyl)-2-butynyl and the like.

The term "haloalkoxyalkyl" refers to a straight chain or branched alkyl as defined hereinbefore substituted with a haloalkoxy, for example 2-chloroethoxymethyl, trifluoromethoxymethyl and the like.

The term "haloalkoxyalkenyl" refers to a straight chain or branched alkenyl as defined hereinbefore substituted with a haloalkoxy, for example 4-(chloromethoxy)-2-butenyl and the like.

The term "haloalkoxyalkynyl" refers to a straight chain or branched alkynyl as defined hereinbefore substituted with a haloalkoxy, for example 4-(2-fluoroethoxy)-2-butynyl and the like.

The term "alkylthioalkyl" refers to a straight chain or branched alkyl as defined hereinbefore substituted with an alkylthio group, for example methylthiomethyl, 3-(isobutylthio)heptyl and the like.

The term "alkylthioalkenyl" refers to a straight chain or branched alkenyl as defined hereinbefore substituted with an alkylthio group, for example 4-(methylthio)-2-butenyl and the like.

The term "alkylthioalkynyl" refers to a straight chain or branched alkynyl as defined hereinbefore substituted with an alkylthio group, for example 4-(ethylthio)-2-butynyl and the like.

The term "haloalkylthioalkyl" refers to a straight chain or branched alkyl as defined hereinbefore substituted with an haloalkylthio group, for example 2-chloroethylthiomethyl, trifluoromethylthiomethyl and the like.

The term "haloalkylthioalkenyl" refers to a straight chain or branched alkenyl as defined hereinbefore substituted with an haloalkylthio group, for example 4-(chloromethylthio)-2-butenyl and the like.

The term "haloalkylthioalkynyl" refers to a straight chain or branched alkynyl as defined hereinbefore substituted The term "dialkoxyphosphorylalkyl" refers to two straight chain or branched alkoxy groups as defined hereinbefore attached to a pentavalent phosphorous atom, containing an oxo substituent, which is in turn attached to an alkyl, for example diethoxyphosphorylmethyl.

The term "oligomer" refers to a low-molecular weight polymer, whose number average molecular weight is typically less than about 5000 g/mol, and whose degree of polymerization (average number of monomer units per chain) is greater than one and typically equal to or less than about 50.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula (I) is shown without a definitive stereochemistry at certain positions. The present invention includes all stereoisomers of Formula (I) and pharmaceutically acceptable salts thereof. Further, mixtures of stereoisomers as well as isolated specific stereoisomers are also included.

During the course of the synthetic procedures used to prepare such compounds, or in using racemization or epimerization procedures known to those skilled in the art, the products of such procedures can be a mixture of stereoisomers.

The invention also encompasses a pharmaceutical composition that is comprised of a compound of Formula (I) in combination with a pharmaceutically acceptable carrier.

Such a composition is comprised of a pharmaceutically acceptable carrier, excipient or diluent, and a non-toxic therapeutically effective amount of a compound of Formula (I) as described above, or an E or Z isomer thereof, syn or anti isomer thereof, an optically pure isomer thereof, or a pharmaceutically acceptable salt thereof.

Moreover, within this embodiment, the invention encompasses a pharmaceutical composition for the treatment of disease by inhibiting the cytochrome retinoic acid 4-hydroxylase enzyme (CYP26), comprising a pharmaceutically acceptable carrier and a non-toxic therapeutically effective amount of compound of Formula (I) as described above or a pharmaceutically acceptable salt thereof.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, komethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid.

The pharmaceutical compositions of the present invention comprise a compound represented by Formula (I) (or E or Z isomer thereof, syn or anti isomer thereof, an optically pure isomer thereof, or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Another example is an N-methyl derivative of a compound, which is susceptible to oxidative metabolism resulting in N-demethylation. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

The term "tautomerization" refers to the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The term "tautomer" as used herein, refers to the compounds produced by the proton shift. Thus, the present invention encompasses the tautomeric moieties like pyrazoles, pyridones and enols, etc.

The term "geometrical isomers" refers to cis-trans isomerism, syn-anti or E/Z isomerism based on the Cahn-Ingold-Prelog system. See March's Advanced Organic Chemistry: Reactions, Mechanisms and Structures, Sixth Edition, Wiley-Interscience, pages 182-195 (2007). The term "geometrical isomers" as used herein, refers to compounds having double bond with an E or Z configuration or cis-trans isomers of monocyclic or fused ring systems.

By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

As used herein, the term "isolated" when applied to the compounds of the present invention, refers to such compounds that are (i) separated from at least some components with which they are associated in nature or when they are made and/or (ii) produced, prepared or manufactured by the hand of man.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof; or purified versions thereof. For example, the term "biological sample" refers to any solid or fluid sample obtained from, excreted by or secreted by any living organism, including single-celled micro organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, scrum, urine, bile, seminal fluid, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

DETAILED DESCRIPTION OF CERTAIN PREFERRED EMBODIMENTS

Numerous diseases and conditions responsible for significant morbidity as well as mortality have as an underlying disease mechanism the inappropriate or excessive production of fibrous connective tissue, a process generally known as fibrosis. Such diseases and conditions include fibrotic liver disease, cirrhosis, cardiac fibrosis, pancreatic fibrosis and lung fibrosis including idiopathic pulmonary fibrosis. In addition to these, numerous other conditions and diseases exhibit a fibrotic component, including but not limited to hepatic ischemia-reperfusion injury, cerebral infarction, ischemic heart disease, heart failure and renal disease including renal fibrosis. Compounds embodied herein and pharmaceutical compositions comprising them are useful for the prevention or treatment of such conditions and diseases.

In addition, effects on dysproliferative diseases such as cancer and skin diseases are also benefits of the compounds herein. In one embodiment, compounds embodied herein are useful for the treatment of prostate cancer. In another embodiment, compounds are useful for the treatment of breast cancer. In another embodiment, compounds are useful for the treatment of ovarian cancer. In another embodiment, compounds of the invention are also useful for prevention and treatment of other cancerous and precancerous conditions, including, for example, premalignant and malignant hyperproliferative diseases such as cancers of the breast, skin, prostate, colon, bladder, cervix, uterus, stomach, lung, esophagus, blood and lymphatic system, larynx, oral cavity, metaplasias, dysplasias, neoplasias, leukoplakias and papillomas of the mucous membranes, and in the treatment of Kaposi's sarcoma. In addition, inventive compounds can also be used as agents to treat diseases of the eye, including, for example, proliferative vitreoretinopathy, retinal detachment, corneopathies such as dry eye, as well as in the treatment and prevention of various cardiovascular diseases, including, without limitation, diseases associated with lipid metabolism such as dyslipidemias, prevention of post-angioplasty restenosis and as an agent to increase the level of circulation tissue plasminogen activator. Other uses include the prevention and treatment of conditions and diseases associated with human papilloma virus (HPV), including warts, various inflammatory diseases such as pulmonary fibrosis, ileitis, colitis and Crohn's disease, neurodegenerative diseases such as Alzheimer's disease, Parkinson's disease and stroke, improper pituitary function, including insufficient production of growth hormone, modulation of apoptosis, including both the induction of apoptosis, restoration of hair growth, including combination therapies with the present compounds and other agents such as minoxidil, diseases associated with the immune systems, including use of the present compounds as immunosuppressant and immunostimulants, modulation of organ transplant rejection and facilitation of wound healing, including modulation of chelosis. Compounds have also been discovered to be useful in treating type II non-insulin dependent diabetes mellitus (NIDDM).

Furthermore, compounds of the invention are also useful for the treatment of various skin diseases, such as actinic keratoses, arsenic keratoses, inflammatory and non-inflammatory acne, psoriasis, ichthyoses, keratinization and hyperproliferative disorders of the skin, eczema, atopic dermatitis, Darriers disease and lichen planus; for preventing, treating, and reversal of glucocorticoid, age, and photo damage to the skin. Ichthyoses includes various forms of ichthyosis, such as but not limited to ichthyosis vulgaris, lamellar ichthyosis, X-linked ichthyosis, congenital ichthyosiform erythroderma, epidermolytic hyperkeratosis (bullous ichthyosis), harlequin-type ichthyosis, ichthyosis bullosa of Siemens, ichthyosis hystrix, Curth-Macklin type, hystrix-like ichthyosis with deafness, lamellar ichthyosis, type 1, lamellar ichthyosis, type 2, lamellar ichthyosis, type 3 lamellar ichthyosis, type 4, lamellar ichthyosis, type 5, and autosomal recessive congenital ichthyosis.

The present invention is also directed to treatment of non-malignant tumors and other disorders involving inappropriate cell or tissue growth by administering a therapeutically effective amount of an agent of the invention. For example, it is contemplated that the invention is useful for the treatment of arteriovenous (AV) malformations, particularly in intracranial sites. The invention may also be used to treat psoriasis, a dermatologic condition that is characterized by inflammation and vascular proliferation; benign prostatic hypertrophy, a condition associated with inflammation and possibly vascular proliferation; and cutaneous fungal infections. Treatment of other hyperproliferative disorders is also contemplated. The agents may also be used topically to remove warts, birthmarks, moles, nevi, skin tags, lipomas, angiomas including hemangiomas, and other cutaneous lesions for cosmetic or other purposes.

Compounds embodied herein and pharmaceutical compositions comprising them are useful for the prevention or treatment of such conditions and diseases.

Compounds of this invention include those generally set forth above and described specifically herein, and are illustrated in part by the various classes, subgenera and species disclosed herein.

Additionally, the present invention provides pharmaceutically acceptable derivatives of the inventive compounds, and methods of treating a subject using these compounds, pharmaceutical compositions thereof, or either of these in combination with one or more additional therapeutic agents.

1) General Description of Compounds of the Invention

In one embodiment, compound s useful for the purposes described herein are represented by formula (I)

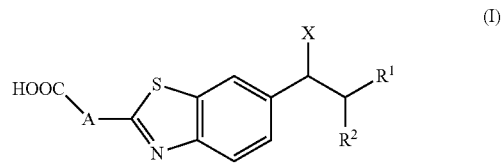

or an E or Z isomer thereof, syn or anti isomer thereof, an optically pure isomer thereof, or pharmaceutically acceptable salt thereof, wherein:

X is a triazole, which is optionally substituted with one or more independent $R^5$ substituents;

$R^1$ and $R^2$ are each independently hydrogen or lower alkyl;

A is

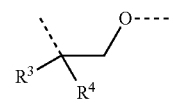

or an aryl, either of which is optionally substituted with one or more independent $R^5$ substituents;

$R^3$ and $R^4$ are each independently hydrogen or lower alkyl which is optionally substituted with one or more $R^5$ substituents; or $R^3$ with $R^4$, taken together with the carbon atom to which they are attached, form a carbonyl or a 3-10 membered saturated or unsaturated monocyclic or polycyclic ring, wherein said ring is optionally substituted with one or more $R^5$;

each occurrence of $R^5$ is independently hydrogen, halogen, cyano, hydroxy, nitro, —$SO_2NR^6R^7$, —$CONR^6R^7$ or —$NR^6R^7$, haloalkyl, or lower alkyl group; and $R^6$ and $R^7$ are each independently hydrogen or a lower alkyl group.

In one embodiment, when A is aryl, $R^1$ and $R^2$ are each independently hydrogen or lower alkyl. In one embodiment, when A is aryl, $R^1$ and $R^2$ are each lower alkyl. In one embodiment, when A is unsubstituted aryl, $R^1$ and $R^2$ are each lower alkyl. In one embodiment, when A is substituted aryl, $R^1$ and $R^2$ are each lower alkyl.

In another embodiment, each occurrence of $R^5$ is independently hydrogen, halogen, cyano, hydroxy, nitro or a lower alkyl group.

In another embodiment, a compound is represented by Formula (I), or a pharmaceutically acceptable salt thereof, wherein X is an optionally substituted triazolyl and the other variables are as described above.

In another embodiment, triazolyl includes 1,2,4-triazolyl and 1,2,3-triazolyl moieties, which may be bound as 1,2,4-triazol-1-yl; 1,2,4-triazol-4-yl, 1,2,3-triazol-1-yl or 1,2,3-triazol-2-yl moieties.

In one embodiment, $R^3$ and $R^4$ taken together with the carbon atom to which they are attached, form a 3-membered monocyclic ring. In one embodiment, $R^3$ and $R^4$ taken together with the carbon atom to which they are attached, form a 4-membered monocyclic ring. In one embodiment, $R^3$ and $R^4$ taken together with the carbon atom to which they are attached, form a 5-membered monocyclic ring. In one embodiment, $R^3$ and $R^4$ taken together with the carbon atom to which they are attached, form a 6-membered monocyclic ring. In one embodiment, $R^3$ and $R^4$ taken together with the carbon atom to which they are attached, form a 7-membered monocyclic ring. In one embodiment, $R^3$ and $R^4$ taken together with the carbon atom to which they are attached, form an 8-membered monocyclic ring. In one embodiment, $R^3$ and $R^4$ taken together with the carbon atom to which they are attached, form a 9-membered monocyclic ring. In one embodiment, $R^3$ and $R^4$ taken together with the carbon atom to which they are attached, form a 10-membered monocyclic ring. In any of the aforementioned embodiments, the ring may be substituted with one or more $R^5$ substituents.

In another embodiment of the present invention, a compound is represented by Formula (I), or an E or Z isomer thereof, syn or anti isomer thereof, an optically pure isomer thereof, or pharmaceutically acceptable salt thereof, wherein A is aryl, and the other variables are as described above.

In another embodiment of the present invention, a compound is represented by Formula (I), or an E or Z isomer thereof, syn or anti isomer thereof, an optically pure isomer thereof, or pharmaceutically acceptable salt thereof, wherein A is

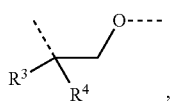

and the other variables are as described above.

In another embodiment, compounds useful for the purposes described herein are represented by Formula (II):

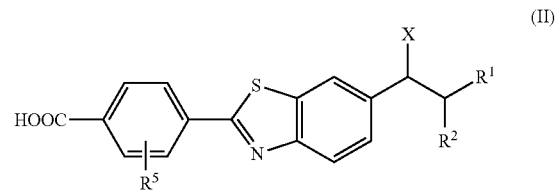

or an E or Z isomer thereof, syn or anti isomer thereof, an optically pure isomer thereof, or pharmaceutically acceptable salt thereof, wherein:

X is a triazole, which is optionally substituted with one or more independent $R^5$ substituents;

$R^1$ and $R^2$ are each independently hydrogen or lower alkyl;

one or more $R^5$ substituents, each independently hydrogen, halogen, cyano, hydroxy, nitro, —$SO_2NR^6R^7$, —$CONR^6R^7$ or —$NR^6R^7$, haloalkyl, or lower alkyl group; and;

$R^6$ and $R^7$ are each independently hydrogen or a lower alkyl group.

In other embodiments, triazole includes 1,2,4-triazole and 1,2,3-triazole, which may be bound as 1,2,4-triazol-1-yl; 1,2,4-triazol-4-yl, 1,2,3-triazol-1-yl or 1,2,3-triazol-2-yl moieties.

In another embodiment, each occurrence of $R^5$ is independently hydrogen, halogen, cyano, hydroxy, nitro or a lower alkyl group.

In one embodiment, when A is aryl, $R^1$ and $R^2$ are each independently hydrogen or lower alkyl. In one embodiment, when A is aryl, $R^1$ and $R^2$ are each lower alkyl. In one embodiment, when A is unsubstituted aryl, $R^1$ and $R^2$ are each lower alkyl. In one embodiment, when A is substituted aryl, $R^1$ and $R^2$ are each lower alkyl.

Nonlimiting examples of compounds of Formula (II) include: 4-(6-(2-ethyl-1-(1H-1,2,4-triazol-1-yl)butyl)benzo[d]thiazol-2-yl)benzoic acid; 4-(6-(2-ethyl-1-(4H-1,2,4-triazol-4-yl)butyl)benzo[d]thiazol-2-yl)benzoic acid; 2-chloro-4-(6-(2-ethyl-1-(1H-1,2,4-triazol-1-yl)butyl)benzo[d]thiazol-2-yl)benzoic acid, 2-chloro-4-(6-(2-ethyl-1-(4H-1,2,4-triazol-4-yl)butyl)benzo[d]thiazol-2-yl)benzoic acid, 4-(6-(2-ethyl-1-(1H-1,2,4-triazol-1-yl)butyl)benzo[d]thiazol-2-yl)-2-(trifluoromethyl)benzoic acid, 4-(6-(2-ethyl-1-(1H-1,2,4-triazol-1-yl)butyl)benzo[d]thiazol-2-yl)-2-fluorobenzoic acid, 4-(6-(2-ethyl-1-(4H-1,2,4-triazol-4-yl)butyl)benzo[d]thiazol-2-yl)-2-(trifluoromethyl)benzoic acid, and 4-(6-(2-ethyl-1-(4H-1,2,4-triazol-4-yl)butyl)benzo[d]thiazol-2-yl)-2-fluorobenzoic acid.

In another embodiment, a compound is represented by Formula (I), or an E or Z isomer thereof, syn or anti isomer thereof, an optically pure isomer thereof, or pharmaceutically acceptable salt thereof, wherein A is

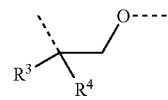

and the other variables are as described above.

In another embodiment, compounds useful for the purposes described herein are represented by Formula (III):

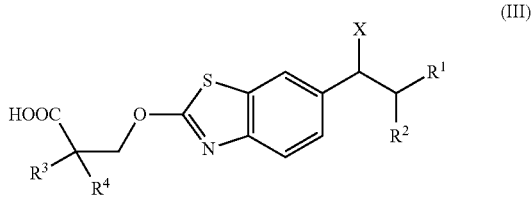
(III)

or an E or Z isomer thereof, syn or anti isomer thereof, an optically pure isomer thereof, or pharmaceutically acceptable salt thereof, and wherein:

X is a triazole, which is optionally substituted with one or more independent $R^5$ substituents;

$R^1$ and $R^2$ are each independently hydrogen or lower alkyl;

$R^3$ and $R^4$ are each independently hydrogen or lower alkyl; or $R^3$ with $R^4$, taken together with the carbon atom to which they are attached, form a carbonyl or a 3-10 membered saturated or unsaturated monocyclic or polycyclic ring, wherein said ring is optionally substituted with one or more $R^5$;

each occurrence of $R^5$ is independently hydrogen, halogen, cyano, hydroxy, nitro, —$SO_2NR^6R^7$, —$CONR^6R^7$ or —$NR^6R^7$, haloalkyl, or lower alkyl group; and $R^6$ and $R^7$ are each independently hydrogen or a lower alkyl group.

In other embodiments, triazole includes 1,2,4-triazole and 1,2,3-triazole, which may be bound as 1,2,4-triazol-1-yl; 1,2,4-triazol-4-yl, 1,2,3-triazol-1-yl or 1,2,3-triazol-2-yl moieties.

In another embodiment, each occurrence of $R^5$ is independently hydrogen, halogen, cyano, hydroxy, nitro or a lower alkyl group.

In other embodiments, $R^3$ and $R^4$ taken together with the carbon atom to which they are attached, form a 3-membered, 4-membered, 5-membered, 6-membered, 7-membered, 8-membered, 9-membered, or 10-membered ring. In certain embodiments, the ring is a monocyclic ring. In certain embodiments, the ring is a bicyclic ring. In certain embodiments the ring is saturated. In certain embodiments the ring is unsaturated. In any of the foregoing embodiments, the ring may be optionally substituted with one or more $R^5$ substituents.

Non-limiting examples of compounds of Formula (III) include: (((6-(2-ethyl-1-(1H-1,2,4-triazol-1-yl)butyl)benzo[d]thiazol-2-yl)oxy)methyl)cyclohexanecarboxylic acid; 1-(((6-(2-ethyl-1-(1H-1,2,4-triazol-1-yl)butyl)benzo[d]thiazol-2-yl)oxy)methyl)cyclopentanecarboxylic acid; 1-(((6-(2-ethyl-1-(4H-1,2,4-triazol-4-yl)butyl)benzo[d]thiazol-2-yl)oxy)methyl)cyclohexanecarboxylic acid; 1-(((6-(2-ethyl-1-(4H-1,2,4-triazol-4-yl)butyl)benzo[d]thiazol-2-yl)oxy)methyl)cyclopentanecarboxylic acid; 3-((6-(2-ethyl-1-(1H-1,2,4-triazol-1-yl)butyl)benzo[d]thiazol-2-yl)oxy)-2,2-dimethylpropanoic acid; 3-((6-(2-ethyl-1-(4H-1,2,4-triazol-4-yl)butyl)benzo[d]thiazol-2-yl)oxy)-2,2-dimethylpropanoic acid; 1-(((6-(2-ethyl-1-(1H-1,2,4-triazol-1-yl)butyl)benzo[d]thiazol-2-yl)oxy)methyl)cyclobutanecarboxylic acid; 1-(((6-(2-ethyl-1-(1H-1,2,4-triazol-1-yl)butyl)benzo[d]thiazol-2-yl)oxy)methyl)cycloheptanecarboxylic acid; 1-(((6-(2-ethyl-1-(1H-1,2,4-triazol-1-yl)butyl)benzo[d]thiazol-2-yl)oxy)methyl)cyclopropanecarboxylic acid; 1-(((6-(2-ethyl-1-(4H-1,2,4-triazol-4-yl)butyl)benzo[d]thiazol-2-yl)oxy)methyl)cyclobutanecarboxylic acid; 1-(((6-(2-ethyl-1-(4H-1,2,4-triazol-4-yl)butyl)benzo[d]thiazol-2-yl)oxy)methyl)cycloheptanecarboxylic acid; 1-(((6-(2-ethyl-1-(4H-1,2,4-triazol-4-yl)butyl)benzo[d]thiazol-2-yl)oxy)methyl)cyclopropanecarboxylic acid; 2-ethyl-2-(((6-(2-ethyl-1-(1H-1,2,4-triazol-1-yl)butyl)benzo[d]thiazol-2-yl)oxy)methyl)butanoic acid; and 2-ethyl-2-(((6-(2-ethyl-1-(4H-1,2,4-triazol-4-yl)butyl)benzo[d]thiazol-2-yl)oxy)methyl)butanoic acid.

The compounds of the present invention include compounds represented by Formula (I) above, or a pharmaceutically acceptable salt thereof, and 1) wherein X is a triazole which is optionally substituted with one or more independent $R^5$ substituents; or 2) wherein A is aryl, which is optionally substituted with one or more independent $R^5$ substituents; or 3) wherein A is

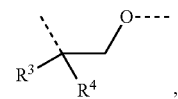

which is optionally substituted with one or more independent $R^5$ substituents; or 4) $R^1$ and $R^2$ are each independently hydrogen or lower alkyl; or 5) $R^1$ and $R^2$ are each independently lower alkyl; or 6) $R^3$ and $R^4$ are each independently hydrogen, lower alkyl or $R^3$ with $R^4$, taken together with the carbon atom to which they are attached, form a 3-10 membered saturated or unsaturated monocyclic or polycyclic ring, wherein said ring is optionally substituted with one or more $R^5$; or 7) $R^5$, is each independently hydrogen, halogen, cyano, hydroxy, nitro, —$SO_2NR^6R^7$, —$CONR^6R^7$ or —$NR^6R^7$, haloalkyl, or lower alkyl group; and $R^6$ and $R^7$ are each independently hydrogen or a lower alkyl group; or 8) wherein X is 1,2,4-triazol-1-yl or 1,2,4-triazol-4-yl; or 9) wherein X is 1,2,3-triazol-1-yl or 1,2,3-triazol-2-yl; or 10) wherein A is a phenyl, which is optionally substituted with one or more independent $R^5$ substituents; or 11) wherein A is

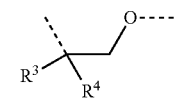

and $R^3$ and $R^4$ are each independently hydrogen; or 12) wherein A is

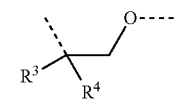

and $R^3$ and $R^4$ are each independently lower alkyl; or 13) wherein A is

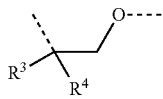

and $R^3$ and $R^4$ are taken together with the carbon atom to which they are attached, form a 3-, 4-, 5-, 6-, 7-, 8-, 9- or 10-membered saturated or unsaturated monocyclic or polycyclic ring, wherein said ring is optionally substituted with one or more $R^5$; or
14) wherein X is a triazole and A is aryl, any which is optionally substituted with one or more independent $R^5$ substituents; or
15) wherein X is a triazole and A is

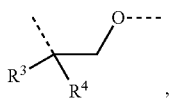, any which is optionally substituted with one or more independent $R^5$ substituents; or
16) wherein X is a triazole and A is aryl, $R^1$ and $R^2$ are each independently lower alkyl, any which is optionally substituted with one or more independent $R^5$ substituents; or
17) wherein X is a triazole and A is

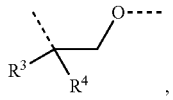, $R^1$ and $R^2$ are each independently lower alkyl, any which is optionally substituted with one or more independent $R^5$ substituents; or
18) wherein X is 1,2,4-triazole-1-yl or 1,2,4-triazole-4-yl, A is aryl, any which is optionally substituted with one or more independent $R^5$ substituents; or
19) wherein X is 1,2,4-triazole-1-yl or 1,2,4-triazole-4-yl, A is

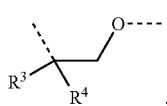, any which is optionally substituted with one or more independent $R^5$ substituents; or
20) wherein X is 1,2,4-triazole-1-yl or 1,2,4-triazole-4-yl, A is aryl, $R^1$ and $R^2$ are each independently lower alkyl, any which is optionally substituted with one or more independent $R^5$ substituents; or
21) wherein X is 1,2,4-triazole-1-yl or 1,2,4-triazole-4-yl, A is

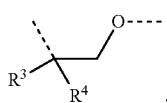, $R^1$ and $R^2$ are each independently lower alkyl, any which is optionally substituted with one or more independent $R^5$ substituents; or
22) wherein X is 1,2,4-triazole-1-yl or 1,2,4-triazole-4-yl, A is phenyl, $R^1$ and $R^2$ are each independently lower alkyl, any which is optionally substituted with one or more independent $R^5$ substituents; or
23) wherein X is 1,2,4-triazole-1-yl or 1,2,4-triazole-4-yl, A is

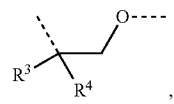, $R^1$ and $R^2$ are each independently lower alkyl, $R^3$ and $R^4$ are each independently lower alkyl, and any which is optionally substituted with one or more independent $R^5$ substituents; or
24) wherein X is 1,2,4-triazole-1-yl or 1,2,4-triazole-4-yl, A is

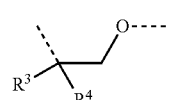, $R^1$ and $R^2$ are each independently lower alkyl, $R^3$ and $R^4$ are each independently methyl, and any which is optionally substituted with one or more independent $R^5$ substituents; or
25) wherein X is 1,2,4-triazole-1-yl or 1,2,4-triazole-4-yl, A is

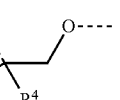, $R^1$ and $R^2$ are each independently lower alkyl, $R^3$ with $R^4$, taken together with the carbon atom to which they are attached, form a 3-10 membered saturated or unsaturated monocyclic or polycyclic ring, and any which is optionally substituted with one or more independent $R^5$ substituents; or
26) wherein X is 1,2,4-triazole-1-yl or 1,2,4-triazole-4-yl, A is $R^1$ and $R^2$ are each independently lower alkyl, $R^3$ with $R^4$, taken together with the carbon atom to which they are attached, form a 4-membered monocyclic ring, and any which is optionally substituted with one or more independent $R^5$ substituents; or
27) wherein X is 1,2,4-triazole-1-yl or 1,2,4-triazole-4-yl, A is

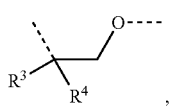

R¹ and R² are each independently lower alkyl, R³ with R⁴, taken together with the carbon atom to which they are attached, form a 5-membered monocyclic ring, and any which is optionally substituted with one or more independent R⁵ substituents; or 28) wherein X is 1,2,4-triazole-1-yl or 1,2,4-triazole-4-yl, A is

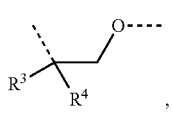

R¹ and R² are each independently lower alkyl, R³ with R⁴, taken together with the carbon atom to which they are attached, form a 6-membered monocyclic ring, and any which is optionally substituted with one or more independent R⁵ substituents; or 29) wherein X is 1,2,4-triazole-1-yl or 1,2,4-triazole-4-yl, A is

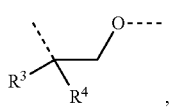

R¹ and R² are each independently lower alkyl, R³ with R⁴, taken together with the carbon atom to which they are attached, form a 7-membered monocyclic ring, and any which is optionally substituted with one or more independent R⁵ substituents; or 30) wherein X is 1,2,4-triazole-1-yl or 1,2,4-triazole-4-yl, A is

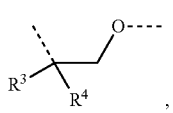

R¹ and R² are each independently ethyl, R³ with R⁴, taken together with the carbon atom to which they are attached, form a 4-membered monocyclic ring, and any which is optionally substituted with one or more independent R⁵ substituents; or 31) wherein X is 1,2,4-triazole-1-yl or 1,2,4-triazole-4-yl, A is

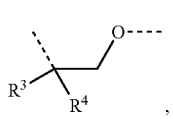

R¹ and R² are each independently ethyl, R³ with R⁴, taken together with the carbon atom to which they are attached, form a 5-membered monocyclic ring, and any which is optionally substituted with one or more independent R⁵ substituents; or 32) wherein X is 1,2,4-triazole-1-yl or 1,2,4-triazole-4-yl, A is

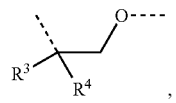

R¹ and R² are each independently ethyl, R³ with R⁴, taken together with the carbon atom to which they are attached, form a 6-membered monocyclic ring, and any which is optionally substituted with one or more independent R⁵ substituents; or 33) wherein X is 1,2,4-triazole-1-yl or 1,2,4-triazole-4-yl, A is

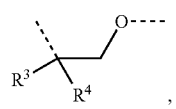

R¹ and R² are each independently ethyl, R³ with R⁴, taken together with the carbon atom to which they are attached, form a 7-membered monocyclic ring, and any which is optionally substituted with one or more independent R⁵ substituents;

and wherein, in each case, the other variables are as defined above for Formula (I).

It will be appreciated that each of the compounds described herein and each of the classes and subclasses of compounds described above (I-III) may be substituted as described generally herein, or may be substituted according to any one or more of the subclasses described above and herein.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I)-(III) under different conditions and may exist as one or a combination of polymorphs of compound of general formula (I)-(III) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric and geometrical isomeric forms, their stereoisomers, their polymorphs, their pharmaceutically acceptable salts their pharmaceutically acceptable solvates and pharmaceutically acceptable compositions containing them. Tautomeric forms of compounds of the present invention include, pyrazoles, pyridones and enols, etc., and geometrical isomers include E/Z isomers of compounds having double bonds and cis-trans isomers of monocyclic or fused ring systems, etc.

2) Pharmaceutical Compositions

In practice, the compounds represented by Formulas (I)-(III), or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formulas (I)-(III), or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formulas (I)-(III). The compounds of Formulas (I)-(III), or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula (I) of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula (I)-(VI), or pharmaceutically acceptable salts thereof, may also be prepared in powder or liquid concentrate form.

Generally, dosage levels on the order of from about 0.01 mg/kg to about 1 50 mg/kg of body weight per day are useful in the treatment of the above indicated conditions, or alternatively about 0.5 mg to about 7 g per patient per day. For example, dermatological diseases and cancers may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

As discussed above this invention provides novel compounds that have biological properties useful for the treatment of any of a number of conditions or diseases in which inhibition of CYP or the activities thereof have a therapeutically useful role. Further description of pharmaceutical compositions is provided herein below.

Accordingly, in another aspect of the present invention, pharmaceutical compositions are provided, which comprise any one or more of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent to treat the same or related indication, or it may be any one of a number of agents undergoing approval in the Food and Drug Administration that ultimately obtain approval for the treatment of any disorder related to fibrosis. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood, or N-demethylation of a compound of the invention where $R^1$ is methyl. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. By way of example, N-methylated pro-drugs of the compounds of the invention are embraced herein.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

In one embodiment, liquid compositions or liquid formulations comprising compounds of the invention are provided that have increased solubility as compared to compounds of the invention dissolved in aqueous buffer such as phosphate-buffered saline. In one embodiment, such liquid compositions with increased solubility are provided by a composition comprising polyethylene glycol, polysorbate or a combination thereof. In one embodiment, the polyethylene glycol is polyethylene glycol 300. In another embodiment the polysorbate is polysorbate 80. In another embodiment the polyethylene glycol is present at about 40% to about 60% (v/v). In another embodiment the polysorbate is present at about 5% to about 15% (v/v). In another embodiment the polyethylene glycol is present at about 50% (v/v). In another embodiment the polysorbate is present at about 10% (v/v). In one formulation, the polyethylene glycol is present at 50% (v/v) together with polysorbate 80 at 10% (v/v). The balance of the solution can be a saline solution, a buffer or a buffered saline solution, such as phosphate-buffered saline. The pH of the solution can be from about pH 5 to about pH 9, and in other embodiments, about from pH 6 to about pH 8. In one embodiment the pH of the buffer is 7.4. In the foregoing embodiments, the compound of the invention is soluble at a concentration higher than in buffer alone, and can be present at about 0.8 to about 10 milligrams per milliliter of solution, or even higher. These formulations offer the preparation of convenient dosing solutions of practical volumes for single dose administration, by any route, in particular a parenteral route. In one embodiment, the route is intravenous, subcutaneous or intraperitoneal. Such compositions with a higher solubility permit achievement of more elevated blood concentrations that provide efficacy when the threshold Cmax (maximal blood concentration after administration) should be achieved for optimal efficacy.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

In other embodiments, solid dosage forms of compounds embodied herein are provided. In some embodiment, such solid dosage forms have improved oral bioavailability. In one embodiment, a formulation is prepared in a solid formulation comprising about 20% (w/w) compound of the invention, about 10-20% (w/w) GLUCIRE® 44/14, about 10-20% (w/w) vitamin E succinate (TPS), 0 to about 60% polyethylene glycol 400, 0 to about 40% Lubrizol, 0 to about 15% Cremophor RH 40 (w/w), and about 1% (w/w) BHT. Formulations containing Cremophor RH 20 are liquid at room temperature but waxy solids at 4 C. The foregoing examples of one or more agents to aid in preparing formulations of inventive compound are merely illustrative and non-limiting.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In other embodiments solid dosage forms are provided. In certain embodiments, such solid dosage forms provide a higher than about a 20% oral bioavailability. As will be shown in the examples below, compounds of the invention can be co-precipitated with one or more agents such as mannitol, a combination of mannitol and lactobionic acid, a combination of mannitol and gluconic acid, a combination of mannitol and methanesulfonic acid, a combination of microcrystalline cellulose and oleic acid or a combination of pregelatinized starch and oleic acid. The foregoing examples of one or more agents to aid in preparing formulations of inventive compound are merely illustrative and non-limiting. Non-limiting examples of inventive compounds in such solid dosage forms include The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Formulations for intraocular administration are also included. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects). In non-limiting examples, one or more compounds of the invention may be formulated with at least one cytokine, growth factor or other biological, such as an interferon, e.g., alpha interferon, or with at least another small molecule compound. Non-limiting examples of pharmaceutical agents that may be combined therapeutically with compounds of the invention include: antivirals and antifibrotics such as interferon alpha, combination of interferon alpha and ribavirin, Lamivudine, Adefovir dipivoxil and interferon gamma; anticoagulants such as heparin and warfarin; antiplatelets e.g., aspirin, ticlopidine and clopidogrel; other growth factors involved in regeneration, e.g., VEGF and FGF and mimetics of these growth factors; antiapoptotic agents; and motility and morphogenic agents.

In certain embodiments, the pharmaceutical compositions of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

3) Research Uses, Clinical Uses, Pharmaceutical Uses and Methods of Treatment

In another embodiment, the aforementioned Formulae (I-III) and compounds have anti-fibrotic activities and thus are useful for the prevention, treatment or lessening of the severity of a condition or disease associated with or characterized by increased, excessive or inappropriate fibrosis. Such conditions and diseases include but are not limited to fibrotic liver disease, hepatic ischemia-reperfusion injury, cerebral infarction, pancreatic fibrosis, ischemic heart disease, neurodegenerative disease, renal disease or lung (pulmonary) fibrosis. In certain embodiments, the method is for treating or lessening the severity of a disease or condition selected from liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke; cerebrovascular disease; myocardial ischemia; atherosclerosis; renal failure; renal fibrosis or idiopathic pulmonary fibrosis. In certain exemplary embodiments, the method is for the treatment of wounds for acceleration of healing; vascularization of a damaged and/or ischemic organ, transplant or graft; amelioration of ischemia/reperfusion injury in the brain, heart, liver, kidney, and other tissues and organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; amyotrophic lateral sclerosis, muscular dystrophy, pancreatitis, scleroderma, chronic obstructive pulmonary disease, emphysema, diabetes mellitus, multiple sclerosis, trauma to the central nervous system, and hereditary neurodegenerative disorders including the leukodystrophies such as metachromatic leukodystrophy, Refsum's disease, adrenoleukodystrophy, Krabbe's disease, phenylketonuria, Canavan disease, Pelizaeus-Merzbacher disease and Alexander's disease.

Furthermore, compounds of the invention are also useful for the treatment of various skin diseases, such as actinic keratoses, arsenic keratoses, inflammatory and non-inflammatory acne, psoriasis, ichthyoses, keratinization and hyperproliferative disorders of the skin, eczema, atopic dermatitis, Darriers disease and lichen planus; for preventing, treating, and reversal of glucocorticoid, age, and photo damage to the skin. Such damage can manifest as lines and wrinkling of the face and other parts of the body, including crow's feet, which are of particular concern to many individuals. Ichthyoses includes various forms of ichthyosis, such as but not limited to ichthyosis vulgaris, lamellar ichthyosis, X-linked ichthyosis, congenital ichthyosiform erythroderma, epidermolytic hyperkeratosis (bullous ichthyosis), harlequin-type ichthyosis, ichthyosis bullosa of Siemens, ichthyosis hystrix, Curth-Macklin type, hystrix-like ichthyosis with deafness, lamellar ichthyosis, type 1, lamellar ichthyosis, type 2, lamellar ichthyosis, type 3 lamellar ichthyosis, type 4, lamellar ichthyosis, type 5, and autosomal recessive congenital ichthyosis.

In another embodiment, compounds of the invention, typically but not limited to compounds of formulae (I-III), are also useful for prevention and treatment of cancerous and precancerous conditions, including, for example, premalignant and malignant hyperproliferative diseases such as cancers of the breast, skin, prostate, colon, bladder, cervix, uterus, stomach, lung, esophagus, blood and lymphatic system, larynx, oral cavity, metaplasias, dysplasias, neoplasias, leukoplakias and papillomas of the mucous membranes, and in the treatment of Kaposi's sarcoma. In one embodiment, prevention or treatment of cancer of the prostate, are uses of the compounds embodied herein. In addition, inventive compounds can also be used as agents to treat diseases of the eye, including, for example, proliferative vitreoretinopathy, retinal detachment, corneopathies such as dry eye, as well as in the treatment and prevention of various cardiovascular diseases, including, without limitation, diseases associated with lipid metabolism such as dyslipidemias, prevention of post-angioplasty restenosis and as an agent to increase the level of circulation tissue plasminogen activator. Other uses include the prevention and treatment of conditions and diseases associated with human papilloma virus (HPV), including warts, various inflammatory diseases such as pulmonary fibrosis, ileitis, colitis and Crohn's disease, neurodegenerative diseases such as Alzheimer's disease, Parkinson's disease and stroke, improper pituitary function, including insufficient production of growth hormone, modulation of apoptosis, including both the induction of apoptosis, restoration of hair growth, including combination therapies with the present compounds and other agents such as minoxidil, diseases associated with the immune systems, including use of the present compounds as immunosuppressant and immunostimulants, modulation of organ transplant rejection and facilitation of wound healing, including modulation of chelosis. Compounds are also useful in treating type II non-insulin dependent diabetes mellitus (NIDDM).

With regard to treatment and prevention of dysproliferative disorders, inventive compounds are useful in other cases where abnormal or excessive cellular proliferation is the cause of pathology, such as in dysproliferative diseases including cancer, inflammatory joint and skin diseases such as rheumatoid arthritis, and neovascularization in the eye as a consequence of diabetic retinopathy, suppression of cellular proliferation is a desired goal in the treatment of these and other conditions. In either case, therapy to promote or suppress proliferation may be beneficial locally but not systemically, and for a particular duration, and proliferation-modulating therapies must be appropriately applied. Compounds of the invention are beneficial for the treatment of cancer and other dysproliferative diseases and conditions.

Conditions and diseases amenable to prophylaxis or treatment with the compounds of the invention include but are not limited to those in which abnormal vascular or cellular proliferation occurs. Such conditions and diseases include as in dysproliferative diseases including cancer and psoriasis, various inflammatory diseases characterized by proliferation of cells such as atherosclerosis and rheumatoid arthritis, and neovascularization in the eye as a consequence of diabetic retinopathy, suppression of cellular proliferation is a desired goal in the treatment of these and other conditions. As certain of the compounds of the invention have been found to possess antiproliferative activity on cells, as well as antiangiogenic activity, both activities may be beneficial in the treatment of, for example, solid tumors, in which both the dysproliferative cells and the enhanced tumor vasculature elicited thereby are targets for inhibition by the agents of the invention. In either case, therapy to promote or suppress proliferation may be beneficial locally but not systemically, and for a particular duration, and proliferation-modulating therapies must be appropriately applied. The invention embraces localized delivery of such compounds to the affected tissues and organs, to achieve a particular effect.

Non-limiting examples of cancers, tumors, malignancies, neoplasms, and other dysproliferative diseases that can be treated according to the invention include leukemias such as myeloid and lymphocytic leukemias, lymphomas, myeloproliferative diseases, and solid tumors, such as but not limited to sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The present invention is also directed to treatment of non-malignant tumors and other disorders involving inappropriate cell or tissue growth by administering a therapeutically effective amount of an agent of the invention. For example, it is contemplated that the invention is useful for the treatment of arteriovenous (AV) malformations, particularly in intracranial sites. The invention may also be used to treat psoriasis, a dermatologic condition that is characterized by inflammation and vascular proliferation; benign prostatic hypertrophy, a condition associated with inflammation and possibly vascular proliferation; and cutaneous fungal infections. Treatment of other hyperproliferative disorders is also contemplated. The agents may also be used topically to remove warts, birthmarks, moles, nevi, skin tags, lipomas, angiomas including hemangiomas, and other cutaneous lesions for cosmetic or other purposes.

As noted above, other uses of the compounds herein include intentional ablation or destruction of tissues or organs in a human or animal, for example, in the area of animal husbandry, and in the field of reproductive biology, to reduce the number of developing embryos; as an abortifacient, and as a means to achieve a biochemical castration, particularly for livestock and domesticated animals such as pets.

As mentioned above, vascularization of the vitreous humor of the eye as a consequence of diabetic retinopathy is a major cause of blindness, and inhibition of such vascularization is desirable. Other conditions in which vascularization is undesirable include certain chronic inflammatory diseases, in particular inflammatory joint and skin disease, but also other inflammatory diseases in which a proliferative response occurs and is responsible for part of all of the pathology. For example, psoriasis is a common inflammatory skin disease characterized by prominent epidermal hyperplasia and neovascularization in the dermal papillae. Proliferation of smooth muscle cells, perhaps as a consequence of growth factors, is a factor in the narrowing and occlusion of the macrovasculature in atherosclerosis, responsible for myocardial ischemia, angina, myocardial infarction, and stroke, to name a few examples. Peripheral vascular disease and arteriosclerosis obliterans comprise an inflammatory component.

Moreover, localized ablation of tissues or even organs using antiproliferative or antiangiogenic compounds as characterized herein may find use in treatment of certain central nervous system diseases or conditions which otherwise may require dangerous invasive procedures; removal of cosmetically undesirable cutaneous lesions are further targets for the antiproliferative agents of the invention. In reproductive biology, such antiproliferative agents may be used as abortifacients or for non-surgical castration, particularly for use in livestock and domesticated animals. These are also merely illustrative of the uses of the instant agents.

In another aspect, the present invention is directed to the treatment and prevention of chronic obstructive pulmonary diseases. Chronic obstructive pulmonary disease (COPD) is estimated to affect 32 million persons in the United States and is the fourth leading cause of death in this country. Patients typically have symptoms of both chronic bronchitis and emphysema, but the classic triad also includes asthma. Most of the time COPD is secondary to tobacco abuse, although cystic fibrosis, alpha-1 antitrypsin deficiency, bronchiectasis, and some rare forms of bullous lung diseases may be causes as well. The invention is directed to all such causes of COPD.

Patients with COPD are susceptible to many insults that can lead rapidly to an acute deterioration superimposed on chronic disease. Quick and accurate recognition of these patients along with aggressive and prompt intervention may be the only action that prevents frank respiratory failure.

Pathophysiology:

COPD is a mixture of 3 separate disease processes that together form the complete clinical and pathophysiological picture. These processes are chronic bronchitis, emphysema and, to a lesser extent, asthma. Each case of COPD is unique in the blend of processes; however, 2 main types of the disease are recognized.

Chronic Bronchitis.

In this type, chronic bronchitis plays the major role. Chronic bronchitis is defined by excessive mucus production with airway obstruction and notable hyperplasia of mucus-producing glands. Damage to the endothelium impairs the mucociliary response that clears bacteria and mucus. Inflammation and secretions provide the obstructive component of chronic bronchitis. In contrast to emphysema, chronic bronchitis is associated with a relatively undamaged pulmonary capillary bed. Emphysema is present to a variable degree but usually is centrilobular rather than panlobular. The body responds by decreasing ventilation and increasing cardiac output. This V/Q mismatch results in rapid circulation in a poorly ventilated lung, leading to hypoxemia and polycythemia.

Eventually, hypercapnia and respiratory acidosis develop, leading to pulmonary artery vasoconstriction and cor pulmonale. With the ensuing hypoxemia, polycythemia, and increased $CO_2$ retention, these patients have signs of right heart failure and are known as "blue bloaters."

Emphysema.

The second major type is that in which emphysema is the primary underlying process. Emphysema is defined by destruction of airways distal to the terminal bronchiole. Physiology of emphysema involves gradual destruction of alveolar septae and of the pulmonary capillary bed, leading to decreased ability to oxygenate blood. The body compensates with lowered cardiac output and hyperventilation. This V/Q mismatch results in relatively limited blood flow through a fairly well oxygenated lung with normal blood gases and pressures in the lung, in contrast to the situation in blue bloaters. Because of low cardiac output, however, the rest of the body suffers from tissue hypoxia and pulmonary cachexia. Eventually, these patients develop muscle wasting and weight loss and are identified as "pink puffers."

In the US, two thirds of men and one fourth of women have emphysema at death. Approximately 8 million people have chronic bronchitis and 2 million have emphysema. COPD is the fourth leading cause of death in the United States, affecting 32 million adults. Men are more likely to have COPD than women, and COPD occurs predominantly in individuals older than 40 years.

History:

Patients with COPD present with a combination of signs and symptoms of chronic bronchitis, emphysema, and asthma. Symptoms include worsening dyspnea, progressive exercise intolerance, and alteration in mental status. In addition, some important clinical and historical differences can exist between the types of COPD. In the chronic bronchitis group, classic symptoms include the following: productive cough, with progression over time to intermittent dyspnea; frequent and recurrent pulmonary infections; and progressive cardiac/respiratory failure over time, with edema and weight gain. In the emphysema group, the history is somewhat different and may include the following set of classic symptoms: a long history of progressive dyspnea with late onset of nonproductive cough; occasional mucopurulent relapses; and eventual cachexia and respiratory failure.

Causes:

In general, the vast majority of COPD cases are the direct result of tobacco abuse. While other causes are known, such as alpha-1 antitrypsin deficiency, cystic fibrosis, air pollution, occupational exposure (e.g., firefighters), and bronchiectasis, this is a disease process that is somewhat unique in its direct correlation to a human activity. The present invention is directed to benefiting COPD regardless of the cause or pathogenic mechanisms.

Thus, the present invention is directed in one aspect to the treatment and prevention of chronic obstructive pulmonary disease as described above. COPD includes, by way of non-limiting example, emphysema, chronic bronchitis and chronic asthma. Such conditions may arise from, among other etiologies, cigarette smoking and other types of exposure to tobacco smoke including second-hand smoke.

While the inventors have no duty to disclose the mechanism by which compounds embodied here operate and are not limited by that disclosure, the inventors herein have found that compounds that inhibit the activity of cytochrome P450, and in particular retinoic acid 4-hydroxylase, also called CYP26, have been found to be beneficial for the purposes described herein. Pharmaceutical compositions of such compounds, their isomers and pharmaceutically acceptable salts, have been found to be useful for such therapeutic purposes. Described herein are non-limiting examples of inhibitors of cytochrome P450 useful for these purposes, but the selections described are merely illustrative and not intending to be limiting to the use of CYP26 inhibition in general to benefit patients with the aforementioned diseases.

Cytochrome P450 (CYP) is a family of enzymes is a very large and diverse superfamily of hemoproteins found in all domains of life. They use a plethora of both exogenous and endogenous compounds as substrates in enzymatic reactions. Usually they form part of multicomponent electron transfer chains, called P450-containing systems. Among the CYP family is CYP26 (also known as retinoic acid 4-hydroxylase) that metabolizes retinoic acid. Based on the studies described herein, it has been found that inhibiting the activity of the CYP26 in vivo is an effective therapeutic approach to the treatment and prevention of a number of conditions and diseases as described herein. Any means of inhibiting CYP26 is embodied herein for the therapeutic purposes herein. Moreover, any condition, injury or disease modulated by the in-vivo level of all trans retinoic acid (ATRA) is encompassed herein. In certain embodiments, a compound of the invention can be administered to inhibit CYP26 to increase endogenous ATRA, and an exogenous retinoic acid can be administered to further enhance the benefit of any of the conditions and diseases disclosed herein. Furthermore, the compounds embodied herein inhibit the activity of cytochrome P450 (CYP) enzymes. In one embodiment, compounds embodied herein show selectivity at inhibiting CYP26 as compared to other CYP enzymes. In another embodiment, the compound embodied herein are more selective at inhibiting CYP26 than one or more other CYP enzymes, other CYP enzymes including but not limited to CYP1A2, CYP2B6, CYP2C8, CYP2C9, CYP2C19, CYP2D6 and CYP3A4. Other CYP enzymes for which the compounds of the invention show selectivity against include CYP17 and CYP19. More selective means that the IC50 of a compound for inhibiting CYP26 is a smaller value than that of another CYP enzyme. In one embodiment, a compound of the invention is at least 2-fold more selective at inhibiting CYP26 than another CYP enzyme. In one embodiment, a compound of the invention is at least 5-fold more selective at inhibiting CYP26 than another CYP enzyme. In one embodiment, a compound of the invention is at least 10-fold more selective at inhibiting CYP26 than another CYP enzyme. In one embodiment, a compound of the invention is at least 20-fold more selective at inhibiting CYP26 than another CYP enzyme. In one embodiment, a compound of the invention is at least 50-fold more selective at inhibiting CYP26 than another CYP enzyme. In one embodiment, a compound of the invention is at least 100-fold more selective at inhibiting CYP26 than another CYP enzyme. In one embodiment, a compound of the invention is at least 200-fold more selective at inhibiting CYP26 than another CYP enzyme. In one embodiment, a compound of the invention is at least 500-fold more selective at inhibiting CYP26 than another CYP enzyme. In one embodiment, a compound of the invention is at least 1000-fold more selective at inhibiting CYP26 than another CYP enzyme. In one embodiment, a compound of the invention is more selective as described above towards one other CYP enzyme. In one embodiment, a compound of the invention is more selective as described above towards two other CYP enzymes. In one embodiment, a compound of the invention is more selective as described above towards three other CYP enzymes. In one embodiment, a compound of the invention is more selective as described above towards four other CYP enzymes. In one embodiment, a compound of the invention is more selective as described above towards five other CYP enzymes. In one embodiment, a compound of the invention is more selective as described above towards six other CYP enzymes. In one embodiment, a compound of the invention is more selective as described above towards more than six other CYP enzymes.

Non-Limiting Examples of Clinical Uses of Compounds with Anti-Fibrotic Activity

1. Fibrotic Liver Disease:

Liver fibrosis is the scarring response of the liver to chronic liver injury; when fibrosis progresses to cirrhosis, morbid complications can develop. In fact, end-stage liver fibrosis or cirrhosis is the seventh leading cause of death in the United States, and afflicts hundreds of millions of people worldwide; deaths from end-stage liver disease in the United States are expected to triple over the next 10-15 years, mainly due to the hepatitis C epidemic 1. In addition to the hepatitis C virus, many other forms of chronic liver injury also lead to end-stage liver disease and cirrhosis, including other viruses such as hepatitis B and delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency).

Treatment of liver fibrosis has focused to date on eliminating the primary injury. For extrahepatic obstructions, biliary decompression is the recommended mode of treatment whereas patients with Wilson's disease are treated with zinc acetate. In chronic hepatitis C infection, interferon has been used as antiviral therapies with limited response: ~20% when used alone or ~50% response when used in combination with ribavirin. In addition to the low-level of response, treatment with interferon with or without ribavirin is associated with numerous severe side effects including neutropenia, thrombocytopenia, anemia, depression, generalized fatigue and flu-like symptoms, which are sufficiently significant to necessitate cessation of therapy. Treatments for other chronic liver diseases such as hepatitis B, autoimmune hepatitis and Wilson's disease are also associated with many side effects, while primary biliary cirrhosis, primary sclerosing cholangitis and non-alcoholic fatty liver disease have no effective treatment other than liver transplantation.

The advantage of treating fibrosis rather than only the underlying etiology, is that antifibrotic therapies should be broadly applicable across the full spectrum of chronic liver diseases. While transplantation is currently the most effective cure for liver fibrosis, mounting evidence indicates that not only fibrosis, but even cirrhosis is reversible. Unfortunately patients often present with advanced stages of fibrosis and cirrhosis, when many therapies such as antivirals can no longer be safely used due to their side effect profile. Such patients would benefit enormously from effective antifibrotic therapy, because attenuating or reversing fibrosis may prevent many late stage complications such as infection, ascites, and loss of liver function and preclude the need for liver transplantation. The compounds of the invention are beneficial for the treatment of the foregoing conditions, and generally are antifibrotic and/or antiapoptotic agents for this and other organ or tissues.

2. Hepatic Ischemia-Reperfusion Injury:

Currently, transplantation is the most effective therapeutic strategy for liver fibrosis. However, in spite of the significant improvement in clinical outcome during the last decade, liver dysfunction or failure is still a significant clinical problem after transplantation surgery. Ischemia-reperfusion (IR) injury to the liver is a major alloantigen-independent component affecting transplantation outcome, causing up to 10% of early organ failure, and leading to the higher incidence of both acute and chronic rejection. Furthermore, given the dramatic organ shortage for transplantation, surgeons are forced to consider cadaveric or steatotic grafts or other marginal livers, which have a higher susceptibility to reperfusion injury. In addition to transplantation surgery, liver IR injury is manifested in clinical situations such as tissue resections (Pringle maneuver), and hemorrhagic shock.

The damage to the postischemic liver represents a continuum of processes that culminate in hepatocellular injury. Ischemia activates Kupffer cells, which are the main sources of vascular reactive oxygen species (ROS) formation during the initial reperfusion period. In addition to Kupffer cell-induced oxidant stress, with increasing length of the ischemic episode, intracellular generation of ROS by xanthine oxidase and in particular mitochondria may also contribute to liver dysfunction and cell injury during reperfusion. Endogenous antioxidant compounds, such as superoxide dismutase, catalase, glutathione, alphatocopherol, and beta-carotene, may all limit the effects of oxidant injury but these systems can quickly become overwhelmed by large quantities of ROS. Work by Lemasters and colleagues, has indicated that in addition to formation of ROS, intracellular calcium dyshomeostasis is a key contributor to liver IR injury. Cell death of hepatocytes and endothelial cells in this setting is characterized by swelling of cells and their organelles, release of cell contents, eosinophilia, karyolysis, and induction of inflammation, characteristic of oncotic necrosis. More recent reports indicate that liver cells also die by apoptosis, which is morphologically characterized by cell shrinkage, formation of apoptotic bodies with intact cell organelles and absence of an inflammatory response.

Indeed, minimizing the adverse effects of IR injury could significantly increase the number of patients that may successfully undergo liver transplantation. Pharmacologic interventions that reduce cell death and/or enhance organ regeneration represent a therapeutic approach to improve clinical outcome in liver transplantation, liver surgery with vascular exclusion and trauma and can therefore reduce recipient/patient morbidity and mortality. The compounds of the invention are beneficial for the treatment of the foregoing conditions.

3. Cerebral Infarction.

Stroke and cerebrovascular disease are a leading cause of morbidity and mortality in the US: at least 600,000 Americans develop strokes each year, and about 160,000 of these are fatal. Research on the pathophysiological basis of stroke has produced new paradigms for prevention and treatment, but translation of these approaches into improved clinical outcomes has proved to be painfully slow. Preventive strategies focus primarily on reducing or controlling risk factors such as diabetes, hypertension, cardiovascular disease, and lifestyle; in patients with severe stenosis, carotid endarterectomy may be indicated. Cerebral angioplasty is used investigationally, but the high restenosis rates observed following coronary angioplasty suggest this approach may pose unacceptable risk for many patients. Therapeutic strategies focus primarily on acute treatment to reduce injury in the ischemic penumbra, the region of reversibly damaged tissue surrounding an infarct. Thrombolytic therapy has been shown to improve perfusion to the ischemic penumbra, but it must be administered within three hours of the onset of infarction. Several neuroprotective agents that block specific tissue responses to ischemia are promising, but none have yet been approved for clinical use. While these therapeutic approaches limit damage in the ischemic penumbra, they do not address the underlying problem of inadequate blood supply due to occluded arteries. An alternative strategy is to induce formation of collateral blood vessels in the ischemic region; this occurs naturally in chronic ischemic conditions, but stimulation of vascularization via therapeutic angiogenesis has potential therapeutic benefit.

Recent advances in imaging have confirmed the pathophysiological basis of the clinical observations of evolving stroke. Analysis of impaired cerebral blood flow (CBF) in the region of an arterial occlusion supports the hypothesis that a central region of very low CBF, the ischemic core, is irreversibly damaged, but damage in surrounding or intermixed zones where CBF is of less severely reduced, the ischemic penumbra, can be limited by timely reperfusion. Plate recently reviewed the evidence suggesting that therapeutic angiogenesis may be useful for treatment or prevention of stroke. First, analysis of cerebral vasculature in stroke patients showed a strong correlation between blood vessel density and survival and a higher density of microvessels in the ischemic hemisphere compared to the contralateral region. Second, studies in experimental models of cerebral ischemia indicate expression of angiogenic growth factors such as vascular endothelial growth factor (VEGF) or HGF/SF is induced rapidly in ischemic brain tissue. Third, administration of VEGF or HGF/SF can reduce neuronal damage and infarct volume in animal models. Similar evidence provided the rationale for developing therapeutic angiogenesis for treating peripheral and myocardial ischemia, which has been shown to produce clinical improvements in early studies in humans. The compounds of the invention, having similar antifibrotic properties, are beneficial for the treatment of the foregoing conditions.

4. Ischemic heart disease is a leading cause of morbidity and mortality in the US, afflicting millions of Americans each year at a cost expected to exceed $300 billion/year. Numerous pharmacological and interventional approaches are being developed to improve treatment of ischemic heart disease including reduction of modifiable risk factors, improved revascularization procedures, and therapies to halt progression and/or induce regression of atherosclerosis. One of the most exciting areas of research for the treatment of myocardial ischemia is therapeutic angiogenesis. Recent studies support the concept that administration of angiogenic growth factors, either by gene transfer or as a recombinant protein, augments nutrient perfusion through neovascularization. The newly developed, supplemental collateral blood vessels constitute endogenous bypass conduits around occluded native arteries, improving perfusion to ischemic tissue. The compounds of the invention are beneficial for the treatment of the foregoing conditions.

5. Renal Disease.

Chronic renal dysfunction is a progressive, degenerative disorder that ultimately results in acute renal failure and requires dialysis as an intervention, and renal transplantation as the only potential cure. Initiating conditions of renal dysfunction include ischemia, diabetes, underlying cardiovascular disease, or renal toxicity associated with certain chemotherapeutics, antibiotics, and radiocontrast agents. Most end-stage pathological changes include extensive fibrinogenesis, epithelial atrophy, and inflammatory cell infiltration into the kidneys.

Acute renal failure is often a complication of diseases including diabetes or renal ischemia, procedures such as heminephrectomy, or as a side effect of therapeutics administered to treat disease. The widely prescribed anti-tumor drug cis-diamminedichloroplatinum (cisplatin), for example, has side effects that include a high incidence of nephrotoxicity and renal dysfunction, mainly in the form of renal tubular damage that leads to impaired glomerular filtration. Administration of gentamicin, an aminoglycoside antibiotic, or cyclosporin A, a potent immunosuppressive compound, causes similar nephrotoxicity. The serious side effects of these effective drugs restrict their use. The development of agents that protect renal function and enhance renal regeneration after administration of nephrotoxic drugs will be of substantial benefit to numerous patients, especially those with malignant tumors, and may allow the maximal therapeutic potentials of these drugs to be realized. The compounds of the invention are beneficial for the treatment of the renal diseases mentioned above.

6. Lung (Pulmonary) Fibrosis.

Idiopathic pulmonary fibrosis (IPF) accounts for a majority of chronic interstitial lung diseases, and has an estimated incidence rate of 10.7 cases for 100,000 per year, with an estimated mortality of 50-70%. IPF is characterized by an abnormal deposition of collagen in the lung with an unknown etiology. Although the precise sequence of the pathogenic sequelae is unknown, disease progression involves epithelial injury and activation, formation of distinctive subepithelial fibroblast/myofibroblast foci, and excessive extracellular matrix accumulation. The development of this pathological process is preceded by an inflammatory response, often dominated by macrophages and lymphocytes, which is mediated by the local release of chemoattractant factors and upregulation of cell-surface adhesion molecules. Lung injury leads to vasodilatation and leakage of plasma proteins into interstitial and alveolar spaces, as well as activation of the coagulation cascade and deposition of fibrin. Fibroblasts migrate into this provisional fibrin matrix where they synthesize extracellular matrix molecules. In non-pathogenic conditions, excess fibrin is usually degraded by plasmin, a proteinase that also has a role in the activation of matrix metalloproteinases (MMPs). Activated MMPs degrade extracellular matrix and participate in fibrin removal, resulting in the clearance of the alveolar spaces and the ultimate restoration of injured tissues. In pathological conditions, however, these processes can lead to progressive and irreversible changes in lung architecture, resulting in progressive respiratory insufficiency and an almost universally terminal outcome in a relatively short period of time. Fibrosis is the final common pathway of a variety of lung disorders, and in this context, the diagnosis of pulmonary fibrosis implies the recognition of an advanced stage in the evolution of a complex process of abnormal repair. While many studies have focused on inflammatory mechanisms for initiating the fibrotic response, the synthesis and degradation the extracellular matrix represent the central event of the disease. It is this process that presents a very attractive site of therapeutic intervention.

The course of IPF is characterized by progressive respiratory insufficiency, leading to death within 3 to 8 years from the onset of symptoms. Management of interstitial lung disease in general, and in particular idiopathic pulmonary fibrosis, is difficult, unpredictable and unsatisfactory. Attempts have been made to use antiinflammatory therapy to reverse inflammation, relief, stop disease progression and prolong survival. Corticosteroids are the most frequently used antiinflammatory agents and have been the mainstay of therapy for IPF for more than four decades, but the efficacy of this approach is unproven, and toxicities are substantial. No studies have compared differing dosages or duration of corticosteroid treatment in matched patients. Interpretation of therapy efficacy is obscured by several factors including heterogeneous patient populations, inclusion of patients with histologic entities other than usual interstitial pneumonia, lack of objective, validated endpoints, and different criteria for "response." Cytotoxic drugs such as Azathioprine and cyclophosphamide have also being used in combination with low dose oral corticosteroids. The results of such treatments vary from no improvement to significant prolongation of survival. Overall, currently available treatments for lung fibrosis are sub-optimal. Potential new therapies have emerged from the use of animal models of pulmonary fibrosis and recent advances in the cellular and molecular biology of inflammatory reactions. Such therapies involve the use of cytokines, oxidants and growth factors that are elaborated during the fibrotic reaction. Despite the use of newer strategies for treatment, the overall prognosis for patients with interstitial lung disease has had little quantifiable change, and the population survival remains unchanged for the last 30 years. Interferon gamma (IFN) may be effective in the treatment of IPF in some patients but its role is controversial. Literature indicated that IFN-gamma may be involved in small airway disease in silicotic lung. Others showed that IFN gamma mediates, bleomycin-induced pulmonary inflammation and fibrosis. The compounds of the invention are beneficial for the treatment of the foregoing condition, among other fibrotic diseases.

7. Demyelinating Diseases.

Demyelinating diseases are those in which myelin is the primary target. They fall into two main groups: acquired diseases (i.e., multiple sclerosis) and hereditary neurodegenerative disorders (i.e., the leukodystrophies). Although their causes and etiologies are different, they have the same outcome: central nervous system (CNS) demyelination. Without myelin, nerve impulses are slowed or stopped, leading to a constellation of neurological symptoms. Multiple sclerosis (MS) is the most common demyelinating disease, which usually manifests itself between the 20th and 50th years of life. Current estimates are that approximately 2.5 million people worldwide have MS, with between 250,000 and 350,000 cases in the United States, 50,000 cases in Canada, 130,000 cases in Germany, 85,000 cases in the United Kingdom, 75,000 cases in France, 50,000 cases in Italy, and 11,000 cases in Switzerland.

MS attacks the white matter of the CNS. In its classic manifestation (90% of all cases), it is characterized by alternating relapsing/remitting phases with the periods of remission growing shorter over time. Its symptoms include any combination of spastic paraparesis, unsteady gait, diplopia, and incontinence.

Other demyelinating diseases include leukodystrophies: metachromatic leukodystrophy, Refsum's disease, adrenoleukodystrophy, Krabbe's disease, phenylketonuria, Canavan disease, Pelizaeus-Merzbacher disease and Alexander's disease. The first six are storage disorders. The lack or the malfunctioning of an enzyme causes a toxic buildup of chemical substances. In Pelizaeus-Merzbacher disease myelin is never formed (dysmyelination) because of a mutation in the gene that produces a basic protein of CNS myelin. The etiology of Alexander's disease remains largely unknown.

In another embodiment, compounds embodied here are useful for the treatment of breast and ovarian cancer. In 2008, breast cancer caused 458,503 deaths worldwide (13.7% of cancer deaths in women). Breast cancer is more than 100 times more due to delays in diagnosis. In 2004, in the United States, 25,580 new cases of ovarian cancer were diagnosed and 16,090 women died of ovarian cancer. The risk increases with age and decreases with pregnancy. Lifetime risk is about 1.6%, but women with affected first-degree relatives have a 5% risk. Women with a mutated BRCA1 or BRCA2 gene carry a risk between 25% and 60% depending on the specific mutation.

Dysproliferative diseases. Dysproliferative disorders refers in one embodiment to abnormal proliferation of cells, including hyperproliferative disorders, hyperplasia, metaplasia, dysplasia, by way of non-limiting examples, as described below.

Hyperproliferative Disorders. In certain embodiments, compounds and compositions of the invention can be used to treat hyperproliferative disorders, including neoplasms. Examples of hyperproliferative disorders that can be treated by compounds and compositions of the invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

Similarly, other hyperproliferative disorders can also be treated by compounds and compositions of the invention. Examples of such hyperproliferative disorders include, but are not limited to: acute childhood lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignancies, anal cancer, astrocytoma, bile duct cancer, bladder cancer, bone cancer, brain stem glioma, brain tumors, breast cancer, cancer of the renal pelvis and ureter, central nervous system (primary) lymphoma, central nervous system lymphoma, cerebellar astrocytoma, cerebral astrocytoma, cervical cancer, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood cerebral astrocytoma, childhood extracranial germ cell tumors, childhood Hodgkin's disease, childhood Hodgkin's lymphoma, childhood hypothalamic and visual pathway glioma, childhood lymphoblastic leukemia, childhood medulloblastoma, childhood non-Hodgkin's lymphoma, childhood pineal and supratentorial primitive neuroectodermal tumors, childhood primary liver cancer, childhood rhabdomyosarcoma, childhood soft tissue sarcoma, childhood visual pathway and hypothalamic glioma, chronic lymphocytic leukemia, chronic myelogenous leukemia, colon cancer, cutaneous T-cell lymphoma, endocrine pancreas islet cell carcinoma, endometrial cancer, ependymoma, epithelial cancer, esophageal cancer, Ewing's sarcoma and related tumors, exocrine pancreatic cancer, extracranial germ cell tumor, extragonadal germ cell tumor, extrahepatic bile duct cancer, eye cancer, female breast cancer, Gaucher's disease, gallbladder cancer, gastric cancer, gastrointestinal carcinoid tumor, gastrointestinal tumors, germ cell tumors, gestational trophoblastic tumor, hairy cell leukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, kidney cancer, laryngeal cancer, lip and oral cavity cancer, liver cancer, lung cancer, lymphoproliferative disorders, macroglobulinemia, male breast cancer, malignant mesothelioma, malignant thymoma, medulloblastoma, melanoma, mesothelioma, metastatic occult primary squamous neck cancer, metastatic primary squamous neck cancer, metastatic squamous neck cancer, multiple myeloma, multiple myeloma/plasma cell neoplasm, myelodysplastic syndrome, myelogenous leukemia, myeloid leukemia, myeloproliferative disorders, nasal cavity and paranasal sinus cancer, nasopharyngeal cancer, neuroblastoma, non-Hodgkin's lymphoma during pregnancy, nonmelanoma skin cancer, non-small cell lung cancer, occult primary metastatic squamous neck cancer, oropharyngeal cancer, osteo-/malignant fibrous sarcoma, osteosarcoma/malignant fibrous histiocytoma, osteosarcoma/malignant fibrous histiocytoma of bone, ovarian epithelial cancer, ovarian germ cell tumor, ovarian low malignant potential tumor, pancreatic cancer, paraproteinemias, purpura, parathyroid cancer, penile cancer, pheochromocytoma, pituitary tumor, plasma cell neoplasm/multiple myeloma, primary central nervous system lymphoma, primary liver cancer, prostate cancer, rectal cancer, renal cell cancer, renal pelvis and ureter cancer, retinoblastoma, rhabdomyosarcoma, salivary gland cancer, sarcoidosis sarcomas, Sezary syndrome, skin cancer, small cell lung cancer, small intestine cancer, soft tissue sarcoma, squamous neck cancer, stomach cancer, supratentorial primitive neuroectodermal and pineal tumors, T-cell lymphoma, testicular cancer, thymoma, thyroid cancer, transitional cell cancer of the renal pelvis and ureter, transitional renal pelvis and ureter cancer, trophoblastic tumors, ureter and renal pelvis cell cancer, urethral cancer, uterine cancer, uterine Sarcoma, vaginal Cancer, visual pathway and hypothalamic glioma, vulvar cancer, Waldenstrom's macroglobulinemia, Wilms' tumor, and any other hyperproliferative disease, located in an organ system listed above.

In another embodiment, the compounds and compositions of the invention are used to prevent, and/or treat premalignant conditions and to prevent progression to a neoplastic or malignant state, including but not limited to those disorders described above. Such uses are indicated in conditions known to precede or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68-79).

Hyperplasia is a form of controlled cell proliferation, involving an increase in cell number in a tissue or organ, without significant alteration in structure or function. Hyperplastic disorders which can be prevented, and/or treated with compounds and compositions of the invention include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

Metaplasia is a form of controlled cell growth in which one type of adult or fully differentiated cell substitutes for another type of adult cell. Metaplastic disorders which can be prevented, and/or treated with compounds and compositions of the invention include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation. Dysplastic disorders which can be prevented, and/or treated with compounds and compositions of the invention include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis *punctata*, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysical dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be prevented, and/or treated with compounds and compositions of the invention include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

In certain embodiments, the present invention relates to the aforementioned method, wherein said cancer or other dysproliferative disease is selected from the group consisting of leukemias, myeloid leukemias (acute and chronic), lymphocytic leukemias (acute and chronic), lymphomas, myeloproliferative diseases, solid tumors, sarcomas, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In certain embodiments, the present invention relates to the aforementioned method, wherein said cancer or other dysproliferative disease is selected from the group consisting of brain tumors, glioma, diabetic retinopathy, and pancreatic cancers.

In certain embodiments, the present invention relates to the aforementioned method, wherein said cancer or other dysproliferative disease is selected from the group consisting of arteriovenous (AV) malformations, psoriasis, benign prostatic hypertrophy, cutaneous fungal infections, warts, birthmarks, moles, nevi, skin tags, lipomas, angiomas hemangiomas, and cutaneous lesions.

9. Inflammatory Disorders.

Another aspect of the invention related to a method for treating an inflammatory disease or disorder such as rheumatoid arthritis, in which, for example, inappropriate angiogenesis leads to the formation of pannus and associated pathology in a joint, or neovascularization from the retina in diabetic patients leading to blindness.

Rheumatoid arthritis (RA) is a chronic disease, characterized mainly by inflammation of the lining, or synovium, of the joints. It can lead to long-term joint damage, resulting in chronic pain, loss of function and disability. The disease progresses in three stages. The first stage is the swelling of the synovial lining, causing pain, warmth, stiffness, redness and swelling around the joint. Second is the rapid division and growth of cells, or pannus, which causes the synovium to thicken. Because it is a chronic disease, RA continues indefinitely and may never resolve. Frequent flares in disease activity can occur. RA is also a systemic disease, with the potential to affect other organs in the body.

Approximately 2.1 million people in the United States, or 1% of the population, have RA. It can affect anyone, including children, but 70% of individuals with RA are women. Onset usually occurs between 30 and 50 years of age. RA often goes into remission in pregnant women, although symptoms tend to increase in intensity after delivery. RA develops more often than expected the year after giving birth. While women are two to three times more likely to get RA than men, men tend to be more severely affected when afflicted.

Exemplary Assays

Efficacy of the compounds of the invention on the aforementioned disorders and diseases or the potential to be of benefit for the prophylaxis or treatment thereof may be demonstrated in various studies, ranging from biochemical effects evaluated in vitro and effects on cells in culture, to in-vivo models of disease, wherein direct clinical manifestations of the disease can be observed and measured, or wherein early structural and/or functional events occur that are established to be involved in the initiation or progression of the disease. The positive effects of the compounds of the invention have been demonstrated in certain assays and can be assayed in a variety of such assays and models, for a number of diseases and disorders. One skilled in the art can readily determine following the guidance described herein whether a compound of the invention is an inhibitor of CYP26 and is useful therapeutically.

1. Hepatic Disease
   a. Antifibrotic Activity in Hepatic Stellate Cells. Serum starved (activated) LX2 cells (an immortalized human hepatic stellate cell line) that are treated with a compound of the invention will show a decrease in collagen I mRNA expression, as well as expression of other fibrotic marker genes, related to significant antifibrotic activity.
   b. Liver Disease endpoints. The rodent model of thioacetamide (TAA)-induced liver fibrosis and the rat bile duct ligation model of fibrosis shows improvements by the compounds of the invention, in a panel of functional and histological tests: gross morphology, mass, portal pressure, presence of ascites, enzymes (AST, ALT), collagen content, interstitial fibrosis and alpha-smooth muscle actin and MMP-2.
2. Protection Against Renal Dysfunction
   a. Clinical model: arterial occlusion. In a mouse model of transient unilateral renal artery occlusion, male ICR mice are anesthetized and the left renal artery occluded with a microvascular clamp. After 30 minutes, the clamp is removed and the kidney allowed to reperfuse. Ten minutes into reperfusion the nonischemic contralateral kidney is excised. Animals are treated daily with vehicle or compound of the invention until the day of sacrifice. Serum creatinine, BUN and urine protein levels, measured at 1, 4 and 7 days post ischemia are used to determine the ability of compounds of the invention to restore function to injured kidneys. In order to create a more severe renal injury, animals are subjected to 45 minutes of ischemia.
   b. Protection against $HgCl_2$-induced renal injury. In a study mice are injected with a high dose of $HgCl_2$ (7 mg/kg, s.c.) and divided into treatment groups. Animals in the first group receive vehicle or a compound of the invention on the day of toxin injection and daily thereafter for 3 days, and are euthanized on day 4. Blood samples that are collected prior to $HgCl_2$ injection, on day 2 and on day 4 are analyzed for serum creatinine. In the second group, treatment with vehicle or compound begins on the day following toxin injection (i.e., 24 h delayed treatment) and daily thereafter until day 6. Mice are euthanized on day 7. Blood samples collected prior to $HgCl_2$ injection; on day 4 and day 7 are analyzed for serum creatinine and BUN. Serum creatinine, BUN, and development of tubular necrosis are measured to indicate positive clinical activity.
   c. Protection against ureteral obstruction. The effects of the compounds of invention on renal injury secondary to ureteral obstruction are examined in a mouse model of transient unilateral renal artery occlusion. Kidneys from mice subject to unilateral ureteral obstruction for 2 weeks are examined for histological evidence of injury and protection by compound treatment. Immunohistochemical staining is performed for fibronectin, proliferating cell nuclear antigen, and TUNEL (for an assessment of apoptosis). Trichrome staining is also performed to assess the extent of collagen formation as an indication of interstitial fibrosis.
3. Cerebral Infarction/Stroke
   a. Neuroprotective Effects in Brain Tissue. Cerebral infarction is induced in rats by middle cerebral artery occlusion (MCAO) for 24 hr. Test compound or vehicle is administered at −24, 0, and 8 hr. Sections of the brain are then examined for cell death by staining with a tetrazolium compound (2,3,5-triphenyl-2H-tetrazolium chloride, or TTC). Normal rat brains exhibit a red staining due to TTC reduction whereas areas containing dead cells are white.
4. Myocardial Infarction
   a. Ability of the compounds of the invention to inhibit apoptosis in a rat model of myocardial infarction (as mentioned above). Hearts from rats subject to left coronary artery ligation are treated with compound (or vehicle control) by direct injection and 24 hours later sectioned and TUNEL stained. Treatment is associated with a significant reduction in the number of apoptotic nuclei.
   b. Clinical model. In a rat ischemia model, myocardial infarction is induced by anterior descending artery occlusion. The infarction is evident by an increase in positive TUNEL staining, indicating DNA fragmentation in late-stage apoptosis. Treatment with compounds of the invention greatly reduces the extent of TUNEL staining.
5. Transplantation and Organ Preservation
   a. The viability of organs and tissues harvested and transported for transplant is currently optimally maintained by bathing and transport in storage solutions such as the University of Wisconsin (UW) cold storage solution (100 mM $KH_2PO_4$, 5 mM $MgSO_4$ 100 mM potassium lactobionate, 1 mM allopurinol, 3 mM glutathione, 5 mM adenosine, 30 mM raffinose, 50 g/liter of hydroxyethyl starch, 40 units/liter of insulin, 16 mg/liter of dexamethasone, 200,000 units/liter of penicillin, pH 7.4; 320-330 mOsM) (Ploeg R J, Goossens D, Vreugdenhil P, McAnulty J F, Southard J H, Belzer F O. Successful 72-hour cold storage kidney preservation with UW solution. Transplant Proc. 1988 February; 20(1 Suppl 1):935-8.). To further enhance the viability of transplanted organs and tissues, inhibit apoptosis and promote vascularization thereof, one or more compounds of the invention may in included in this or any other storage solution, as well as perfused into the donor or donor organ prior to harvesting, and administered to the recipient systemically and/or locally into the transplanted organ or transplant site.

6. Lung Fibrosis
   a. In order to assess the effects of test compounds on pulmonary fibrosis a well-established mouse model of bleomycin-induced lung injury is used. Male C57BL/6 mice (20-30 g, n=10/group) are treated with bleomycin (0.06 U/20 gram body weight) or saline via intratracheal administration. Bleomycin-treated mice are divided into 2 groups. Compounds of the invention or vehicle is administered daily until sacrifice on day 12. Right lung samples from the mice are then harvested for analysis. Tissues are sectioned and stained with modified Masson's Trichrome and are analyzed for interstitial fibrosis. The Ashcroft scale is used to obtain a numerical fibrotic score with each specimen being scored independently by two histopathologists, and the mean of their individual scores considered as the fibrotic score.

7. Emphysema
   a. The porcine pancreatic elastase (PPE)-induced emphysema murine model can be used. For the induction of emphysema, the protocol described in the literature by Takahashi and colleagues (Takahashi S, Nakamura H, Seki M et al. Reversal of elastase-induced pulmonary emphysema and promotion of alveolar epithelial cell proliferation by simvastatin in mice. Am J Physiol Lung Cell Mol Physiol 2008 May; 294(5):L882-L890) is followed. Porcine pancreatic elastase (PPE) is obtained from Sigma (St. Louis, Mo.; Catalog #E7885) and mice are 8-wk-old male C57BL/6 mice (Charles River Laboratories). Animals are anesthetized and receive 20 μg of PPE in 50 μl of saline by surgical intra-tracheal instillation or 50 μl of saline alone (sham control group) on day 0. The day after PPE-instillation, the mice are randomly divided into two groups and receive daily administration by oral gavage of either test compound in water (final concentration 10 mg/kg qd, group designated "TC"), or water (vehicle control group) in a volume of 100 μL. The administration of compound or vehicle is continued for 3½ weeks. At the end of the experiment, animals are weighed and animals are sacrificed before determining arterial blood gas and isolation of lungs for histo-morphology and histo-immunology. Treatment measures include 1) effects on arterial oxygen levels. Arterial oxygen levels are an indicator of pulmonary function, and several studies have indicated reduced arterial oxygen in patients suffering from COPD and other pulmonary disorders (Celli B R, Cote C G, Lareau S C, Meek P M. Predictors of Survival in COPD: more than just the FEV1. Respir Med 2008 June; 102 Suppl 1:S27-S35). To evaluate the arterial oxygen pressure, blood samples are withdrawn from the abdominal artery and blood gas measurements were performed using a Siemens Rapidlab 248 blood gas analyzer. The arterial oxygen pressure in the test compound treated PPE-exposed animals is significantly higher than the pO2 of vehicle treated animals. 2) To evaluate the effects of test compound on lung architecture, histomorphological analyses are carried out in H&E stained histological sections from paraffin embedded fixed lungs. The mean alveolar diameter is calculated by determining the mean linear intercept (Lm) from the analysis of 5 random fields in 6-10 lung slides in the different treatment groups. Typically, treatment with elastase results in an increase in alveolar diameter from an average of 42.5±1.6 μm in the sham operated animals to 56.5±5.8 μm in the elastase treated vehicle animals (Takahashi S, Nakamura H, Seki M et al. Reversal of elastase-induced pulmonary emphysema and promotion of alveolar epithelial cell proliferation by simvastatin in mice. Am J Physiol Lung Cell Mol Physiol 2008 May; 294(5):L882-L890; Plantier L, Marchand-Adam S, Antico V G et al. Keratinocyte growth factor protects against elastase-induced pulmonary emphysema in mice. Am J Physiol Lung Cell Mol Physiol 2007 November; 293(5):L1230-L1239). Effective test compound will significantly decrease the mean alveolar intercept length (Lm) compared to vehicle treated PPE-exposed mice. This indicates a marked effect of TC on lung architecture.

8. Diabetes Mellitus
   a. Normal CD-1 mice are induced to develop hyperglycemia (diabetes) by i.v. injection with 100 mg/kg streptozotocin (STZ) followed by measurement of blood glucose in a week. The animals are treated with test compound or vehicle daily starting the same day of STZ injection. Glucose samples are taken from the tail vein at day 7 with Ascensia ELITE blood glucose test strips (Bayer), and the blood glucose concentration is determined by glucose meters (Bayer). STZ induced diabetes, as shown by a significant increase in blood glucose levels compared to that in normal mice. Compounds of the invention reduce blood glucose levels.

9. Muscular Dystrophy.
   a. In a genetic murine muscular dystrophy model, two months of intraperitoneal administration of a compound embodied herein can be shown to reduce the elevation in creatine kinase, indicating a beneficial effect on the disease.

10. Amyotrophic Lateral Sclerosis.
    a. In SODG93A mouse model of ALS, daily compound administration starting at age 94 days (when neurofilament degeneration typically occurs) through day 122 can significantly improves hind limb pathology score vs. In addition, a stride test shows improvement in treated animals. Survival of the treated animals is also significantly ($p<0.05$) extended vs. vehicle-treated animals.

11. Dysproliferative Diseases
    a. Breast cancer. To test the efficacy of compounds embodied herein against breast cancer, nude mice carrying human breast cancer lines that are estrogen receptor and Aromatase positive will be used. Cells will be grown in vitro and 2 million will be inoculated in Matrigel (50:50 volume ratio of cells to Matrigel). Cells will be distributed by s.c. injection at the right and left flanks or at the orthotopic sites in 6 to 8 week old athymic nude mice (BALB/c strain) or severe combined immunodeficient mice under anesthesia. Animals will be treated with compound for 4 weeks, at which point animals will be sacrificed and collect blood samples and tumor tissue for the determination of serum and tumor estrogen levels. Tumors will be excised and a portion will be fixed in formalin for subsequent histochemical and immuno-histochemical analysis. The remainder will be snap frozen in liquid nitrogen and stored at −80° C.

12. Photoaging and other skin conditions and diseases. Effects of the compounds embodied here on the rough, scaly skin of various forms of ichthyosis, and the effects of aging including photoaging such as fine lines and wrinkles, including crow's feet, can be evaluated by any of various methods. For example, the effect of a daily or more frequent topical formulation of a compounds of the invention on appearance of skin can be measured by using the Modified Fitzpatrick Wrinkle Scale (MFWS), in which changes in periorbital wrinkle depth can be scored over time. The MFWS scale is: Class 0, No wrinkles, no visible wrinkle, continuous skin line; Class 0.5, very shallow yet visible wrinkles; Class 1, fine wrinkles, visible wrinkles and slight indentations; Class 1.5, visible wrinkles and clear indentation, approx. <1 mm wrinkle depth; Class 2, moderate wrinkles, clearly visible wrinkles, approx. 1 to 2 mm wrinkle depth; Class 2.5, prominent and visible wrinkles, more than approximately 2 mm and less than 3 mm wrinkle depth; and Class 3, deep wrinkles, deep and furrowed wrinkles; more than approx. 3 mm wrinkle depth. In addition to the MFWS, the Physician's Global Assessment Grade can be used to assess the overall improvement in wrinkles changing over time, using a score of Grade 0: Worse; Grade 1: No Change; Grade 2: Slightly Improved; Grade 3: Improved; Grade 4: Much Improved. Furthermore, Subject Self-Assessment and Quality of Life questionnaires can be used to assess the effect of treatment 13. CYP26 inhibition activity. A substrate depletion assay for ATRA metabolism in mouse microsomes is used. Mouse microsomes are produced by Xenotech from the livers of mice treated with ATRA for four days to induce CYP26. ATRA metabolism in these microsomes is tested at a final concentration of 0.1 mg protein/mL in a 100 mM phosphate buffer (pH 7.4) containing an NADPH regenerating system (BD Biosciences catalog #451200 and 451220). The assay is run in a 100 µL reaction volume and stopped with an equal volume of methanol. ATRA concentrations at the beginning and end of incubations are determined using HPLC and LC-MS/MS. The "induced" mouse microsomes have vastly increased CYP26 transcription and ATRA metabolic activity compared to normal microsomes (~100 fold) and ATRA metabolic activity displays classical Michaelis-Menten kinetics with a Km of ~4 nM, which is similar to the Km reported for the human recombinant enzyme (~10 nM).

13. CYP inhibition selectivity assays. Assays for evaluating the extent of inhibition of other CYP enzymes by compounds embodied herein were conducted. Assays were carried out to measure inhibition of CYP1A2, CYP2B6, CYP2C8, CYP2C9, CYP2C19, CYP2D6 and CYP3A4. CYP selectivity assays were performed using commercially available kits according to the manufacturer's instructions or were performed by Life Technologies SelectScreen P450 Profiling service. For CYP1A2, the BD Biosciences high throughput inhibitor screening kit 459500 and the Invitrogen Vivid CYP1A2 Blue screening kit P2863 were used; for CYP2B6, the BD Biosciences high throughput inhibitor screening kit 459220 was used; for CYP2C8, the BD Biosciences high throughput inhibitor screening kit 459320 was used; for CYP2C9, the Invitrogen Vivid CYP2C9 Blue Screening kit P2861 was used; for CYP2C19, the Invitrogen Vivid CYP2C19 Blue Screening kit P2864 was used; for CYP2D6, the Invitrogen Vivid CYP2D6 Cyan Screening kit P2862 was used and for CYP3A4, the Invitrogen Vivid CYP3A4 Blue Screening kit P2858 and Invitrogen Vivid CYP3A4 Green Screening kit P2857 were used.

Pharmaceutical Uses and Methods of Treatment

In certain embodiments, the method involves the administration of a therapeutically effective amount of the compound or a pharmaceutically acceptable derivative thereof to a subject (including, but not limited to a human or animal) in need of it. Subjects for which the benefits of the compounds of the invention are intended for administration include, in addition to humans, livestock, domesticated, zoo and companion animals.

As discussed above this invention provides novel compounds that have biological properties useful for inhibiting CYP26, and reducing fibrosis or dysproliferative conditions. In certain embodiments, the inventive compounds are useful for the treatment of wounds for acceleration of healing (wound healing may be accelerated by promoting cellular proliferation, particularly of vascular cells), normalization of myocardial perfusion as a consequence of chronic cardiac ischemia or myocardial infarction, development or augmentation of collateral vessel development after vascular occlusion or to ischemic tissues or organs, fibrotic diseases, hepatic disease including fibrosis and cirrhosis, lung fibrosis, renal failure, renal fibrosis, cerebral infarction (stroke), diabetes mellitus, and vascularization of grafted or transplanted tissues or organs. Renal conditions for which compounds of the invention may prove useful include: radiocontrast nephropathy; fibrosis secondary to renal obstruction; indication for renal trauma and transplantation; renal failure secondary to chronic diabetes and/or hypertension. Benefit in treatment of amyotrophic lateral sclerosis, diabetes mellitus and muscular dystrophy are also embodied herein. Furthermore, benefits in dysproliferative diseases such as cancer, inflammatory skin diseases, psoriasis, inflammatory joint diseases, among others, are also provided.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, subcutaneously, intradermally, intra-ocularly, topically (as by powders, ointments, or drops), buccally, as an oral or nasal spray, or the like, depending on the severity of the disease or disorder being treated. In certain embodiments, the compounds of the invention may be administered at dosage levels of about 0.001 mg/kg to about 50 mg/kg, preferably from about 0.1 mg/kg to about 10 mg/kg for parenteral administration, or preferably from about 1 mg/kg to about 50 mg/kg, more preferably from about 10 mg/kg to about 50 mg/kg for oral administration, of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Moreover, pharmaceutical compositions comprising one or more compounds of the invention may also contain other compounds or agents for which co-administration with the compound(s) of the invention is therapeutically advantageous. As many pharmaceutical agents are used in the treatment of the diseases and disorders for which the compounds of the invention are also beneficial, any may be formulated together for administration. Synergistic formulations are also embraced herein, where the combination of at least one compound of the invention and at least one other compounds act more beneficially than when each is given alone. Non-limiting examples of pharmaceutical agents that may be combined therapeutically with compounds of the invention include (non-limiting examples of diseases or conditions treated with such combination are indicated in parentheses): antivirals and antifibrotics, such as interferon alpha (hepatitis B, and hepatitis C), combination of interferon alpha and ribavirin (hepatitis C), Lamivudine (hepatitis B), Adefovir dipivoxil (hepatitis B), interferon gamma (idiopathic pulmonary fibrosis, liver fibrosis, and fibrosis in other organs); anticoagulants, e.g., heparin and warfarin (ischemic stroke); antiplatelets e.g., aspirin, ticlopidine and clopidogrel (ischemic stroke); other growth factors involved in regeneration, e.g., VEGF and FGF and mimetics of these growth factors; antiapoptotic agents; and motility and morphogenic agents. All-trans retinoic acid and active analogs are also provided as combination therapy.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a well-established literature of small molecule chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety of combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

General Reaction Procedures:

Unless mentioned specifically, reaction mixtures are stirred using a magnetically driven stirrer bar. An inert atmosphere refers to either dry argon or dry nitrogen. Reactions are monitored either by thin layer chromatography, by proton nuclear magnetic resonance (NMR) or by high-pressure liquid chromatography (HPLC), of a suitably worked up sample of the reaction mixture.

General Work Up Procedures:

Unless mentioned specifically, reaction mixtures are cooled to room temperature or below then quenched, when necessary, with either water or a saturated aqueous solution of ammonium chloride. Desired products are extracted by partitioning between water and a suitable water-immiscible solvent (e.g. ethyl acetate, dichloromethane, diethyl ether). The desired product containing extracts are washed appropriately with water followed by a saturated solution of brine. On occasions where the product containing extract is deemed to contain residual oxidants, the extract is washed with a 10% solution of sodium sulphite in saturated aqueous sodium bicarbonate solution, prior to the aforementioned washing procedure. On occasions where the product containing extract is deemed to contain residual acids, the extract is washed with saturated aqueous sodium bicarbonate solution, prior to the aforementioned washing procedure (except in those cases where the desired product itself had acidic character). On occasions where the product containing extract is deemed to contain residual bases, the extract is washed with 10% aqueous citric acid solution, prior to the aforementioned washing procedure (except in those cases where the desired product itself had basic character). Post washing, the desired product containing extracts are dried over anhydrous magnesium sulphate, and then filtered. The crude products are then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes are combined and concentrated under reduced pressure at an appropriate temperature (generally less than 45° C.) to constant mass.

1) Synthesis of Exemplary Compounds:

Unless otherwise indicated, starting materials are either commercially available or readily accessible through laboratory synthesis by anyone reasonably familiar with the art. Described generally below, are procedures and general guidance for the synthesis of compounds as described generally and in subclasses and species herein. In addition, synthetic guidance can be found in Kinoshita, M. et al. Bull. Chem. Soc. Jpn. 1987, 60, 2151-2162; Natchev, I. A. Tetrahedron 1988, 44, 1511-1522; Almirante, N. et al. Tetrahedron Lett. 1998, 39, 3287; and Bellassoued and Majidi, J. Org. Chem. 1993, 58, 2517-2522; the entire contents of which are hereby incorporated by reference.

Moreover, guidance for the synthesis of the compounds embodied herein may be found in Bioorganic & Medicinal Chemistry 15 (2007) 3692-3702; ARKIVOC 2007 (xiii) 150-154; J. Med. Chem. 784, 1970; J. Org. Chem. 2008, 73, 538-549; Synth. Commun. Vol. 32, No. 22, pp. 3399-3405, 2002; J. Org. Chem. 2007, 72, 8543-8546; J. Org. Chem. 2001, 66, 7945-7950; J. Med. Chem. 2007, 50, 6116-6125; J. Org. Chem. 1993, 58, 7899-7902; Tetrahedron, Vol. 53, No. 33, pp. 11355-11368, 1997; Synthesis 2006, No. 6, 995-998; Tetrahedron Letters 39 (1998) 9347-9350; Synthesis-1986, 620; U.S. patents/applications 0208582; U.S. Pat. Nos. 3,050,520; 4,625,036; 7,192,976; 7,250,437; 7,265,112; WO 2005/073189 or WO2004/058721. Other sources include WO2005/007631, based on PCT/US2004/022282, and in WO2002/03912, based on PCT/US2001/16524.

Synthesis of Exemplary Compounds

Example-1: 3-((6-(2-Ethyl-1-(1H-1,2,4-triazol-1-yl)butyl)benzo[d]thiazol-2-yl)oxy)-2,2-dimethylpropanoic acid Step-1: 1-(2-Aminobenzo[d]thiazol-6-yl)-2-ethylbutan-1-one To a mixture of 1-(4-aminophenyl)-2-ethylbutan-1-one (3.825 g, 20 mmol) and KSCN (7.774 g, 80 mmol) in acetic acid (100 mL) was stirred at RT until a clear solution was obtained. Bromine in acetic acid (10 mL) was added drop wise and the mixture was stirred at RT overnight. Ice was added to cool the reaction mixture to 0° C., basified with ammonium hydroxide and filtered. The filter cake was triturated with 5% methanol in dichloromethane (100 mL) and filtered. The filter cake was washed with dichloromethane (3×100 mL) and the combined filtrate was dried over anhydrous sodium sulfate and evaporated under reduced pressure to afford 1-(2-aminobenzo[d]thiazol-6-yl)-2-ethylbutan-1-one. $^1$H NMR (CDCl$_3$, 300 MHz): δ 0.88 (t, J=7.2 Hz, 6H), 1.50-1.68 (m, 2H), 1.70-1.88 (m, 2H), 3.25-3.38 (m, 1H), 5.71 (br, 2H), 7.56 (d, J=8.4 Hz, 1H), 7.95 (dd, J=8.4, 1.5 Hz, 1H), 8.26 (d, J=1.5 Hz, 1H).

Step-2: 1-(2-Bromobenzo[d]thiazol-6-yl)-2-ethylbutan-1-one

To a mixture of 1-(2-aminobenzo[d]thiazol-6-yl)-2-ethylbutan-1-one (4.1 g, 16.51 mmol), acetonitrile (60 mL) and water (60 mL) at 0° C. was added HBr (48%, 18.7 mL) and the mixture was stirred for 5 min. Sodium nitrite (1.426 g, 20.64 mmol) in water (10 mL) was added slowly at 0° C. and stirred for 15 min. Copper (II) bromide (4.816 g, 20.64 mmol) in water (20 mL) was added and the reaction was allowed to warm to RT and stirred at RT for 2 h. Ethyl acetate was added and the mixture was filtered through a pad of celite. The aqueous layer was extracted with ethyl acetate and the combined ethyl acetate layer was dried over anhydrous sodium sulfate and evaporated under reduced pressure. The crude product was purified by silica gel column chromatography eluting with 0→10% ethyl acetate in hexanes to afford 1-(2-bromobenzo[d]thiazol-6-yl)-2-ethylbutan-1-one. $^1$H NMR (CDCl$_3$, 300 MHz): δ 0.89 (t, J=7.2 Hz, 6H), 1.55-1.67 (m, 2H), 1.75-1.87 (m, 2H), 8.05-8.09 (m, 2H), 8.45 (d, J=0.6 Hz, 1H).

Step-3: Methyl 3-((6-(2-ethylbutanoyl)benzo[d]thiazol-2-yl)oxy)-2,2-dimethylpropanoate To a mixture of 1-(2-bromobenzo[d]thiazol-6-yl)-2-ethylbutan-1-one (937 mg, 3 mmol) and methyl 3-hydroxy-2,2-dimethylpropanoate (475 mg, 3.6 mmol) in THF (20 mL) at −10° C. was added sodium hydride (60%, 144 mg, 3.6 mmol) and the mixture was stirred for 15 min at −10° C. The reaction was allowed to warm to RT and stirred at RT for 2 h. Water was added and extracted with ethyl acetate. The combined organic layers were dried over anhydrous sodium sulfate and evaporated under reduced pressure. The crude product was purified by silica gel column chromatography eluting with 0→10% ethyl acetate in hexanes to afford methyl 3-((6-(2-ethylbutanoyl)benzo[d]thiazol-2-yl)oxy)-2,2-dimethylpropanoate. ¹H NMR (CDCl₃, 300 MHz): δ 0.88 (t, J=7.5 Hz, 6H), 1.34 (s, 6H), 1.54-1.60 (m, 2H), 1.73-1.85 (m, 2H), 3.28-3.35 (m, 1H), 3.71 (s, 3H), 4.63 (s, 2H), 7.71 (d, J=8.7 Hz, 1H), 7.98 (dd, J=8.1 Hz, 1H), 8.29 (d, J=1.5 Hz, 1H). MS (ES+): m/z 364.2 (MH⁺).

Step-4: Methyl 3-((6-(2-ethyl-1-hydroxybutyl)benzo[d]thiazol-2-yl)oxy)-2,2-dimethylpropanoate To a solution of methyl 3-((6-(2-ethylbutanoyl)benzo[d]thiazol-2-yl)oxy)-2,2-dimethylpropanoate (630 mg, 1.73 mmol) in methanol (15 mL) at RT was added sodium borohydride (131 mg, 3.46 mmol) and the mixture was stirred overnight. Water was added and the reaction mixture was evaporated under reduced pressure. The residue was dissolved in water and extracted with ethyl acetate. The combined organic layers were dried over anhydrous sodium sulfate and evaporated under reduced pressure. The crude product was purified by silica gel column chromatography eluting with 0→10% ethyl acetate in hexanes to afford methyl 3-((6-(2-ethyl-1-hydroxybutyl)benzo[d]thiazol-2-yl)oxy)-2,2-dimethylpropanoate. ¹H NMR (CDCl₃, 300 MHz): δ 0.75 (m, 6H), 1.04-1.27 (m, 8H), 1.34-1.54 (m, 2H), 1.71-1.78 (m 1H), 3.64 (s, 3H), 4.51 (s, 2H), 4.63 (d, J=6.3 Hz, 1H), 7.22 (dd, J=8.7, 1.5 Hz, 1H), 7.55 (m, 2H).

Step-5: Methyl 3-((6-(2-ethyl-1-(1H-1,2,4-triazol-1-yl)butyl)benzo[d]thiazol-2-yl)oxy)-2,2-dimethylpropanoate and methyl 3-((6-(2-ethyl-1-(4H-1,2,4-triazol-4-yl)butyl)benzo[d]thiazol-2-yl)oxy)-2,2-dimethylpropanoate A mixture of methyl 3-((6-(2-ethyl-1-hydroxybutyl)benzo[d]thiazol-2-yl)oxy)-2,2-dimethylpropanoate (25 mg, 0.0684 mmol) and carbonylditriazole (25 mg, 0.152 mmol) in acetonitrile (4 mL) was heated to 75° C. and stirred overnight. Water was added and the reaction mixture was evaporated under reduced pressure. To the residue was added water and extracted with dichloromethane. The combined organic layers were dried over anhydrous sodium sulfate and evaporated under reduced pressure. The crude product was purified by silica gel column chromatography eluting with 0→5% methanol in hexanes to afford methyl 3-((6-(2-ethyl-1-(1H-1,2,4-triazol-1-yl)butyl)benzo[d]thiazol-2-yl)oxy)-2,2-dimethylpropanoate. ¹H NMR (CDCl₃, 300 MHz): δ 0.74-0.83 (m, 6H), 1.11-1.29 (m, 10H), 2.51-2.54 (m, 1H), 3.68 (s, 3H), 4.47 (s, 2H), 5.22 (d, J=10.8 Hz, 1H), 7.46 (dd, J=8.4, 1.8 Hz, 1H), 7.60 (d, J=8.4 Hz, 1H), 7.82 (d, J=1.5 Hz, 1H), 7.90 (s, 1H), 8.33 (s, 1H). Continued elution of the column afforded methyl 3-((6-(2-ethyl-1-(4H-1,2,4-triazol-4-yl)butyl)benzo[d]thiazol-2-yl)oxy)-2,2-dimethylpropanoate. ¹H NMR (CDCl₃, 300 MHz): δ 0.76-0.87 (m, 6H), 1.16-1.37 (m, 10H), 2.35-2.39 (m, 1H), 3.68 (s, 3H), 4.44 (s, 2H), 5.17 (d, J=10.8 Hz, 1H), 7.37 (dd, J=8.4, 1.8 Hz, 1H), 7.63 (d, J=8.4 Hz, 1H), 7.69 (d, J=1.5 Hz, 1H), 8.45 (s, 2H).

Step-6: 3-((6-(2-Ethyl-1-(1H-1,2,4-triazol-1-yl)butyl)benzo[d]thiazol-2-yl)oxy)-2,2-dimethylpropanoic acid A mixture of methyl 3-((6-(2-ethyl-1-(1H-1,2,4-triazol-1-yl)butyl)benzo[d]thiazol-2-yl)oxy)-2,2-dimethylpropanoate (10 mg, 0.024 mmol), lithium hydroxide (5 mg, 0.12 mmol) and water (0.5 mL) in dioxane (1 mL) was stirred at 50° C. overnight. The reaction was concentrated, water was added and neutralized to pH 6.5-7 and extracted with dichloromethane. The combined organic layers were dried over anhydrous sodium sulfate and evaporated under reduced pressure. The crude product was purified by silica gel column chromatography eluting with 0→10% methanol in hexanes to afford 3-((6-(2-ethyl-1-(1H-1,2,4-triazol-1-yl)butyl)benzo[d]thiazol-2-yl)oxy)-2,2-dimethylpropanoic acid. ¹H NMR (CDCl₃, 300 MHz): δ 0.74-0.86 (m, 6H), 1.09-1.23 (m, 10H), 2.48-2.58 (m, 1H), 4.55 (s, 2H), 5.23 (d, J=11.1 Hz, 1H), 7.46 (dd, J=6.6, 2.1 Hz, 1H), 5.56 (d, J=8.7 Hz, 1H), 7.81 (d, J=1.8 Hz, 1H), 7.90 (s, 1H), 8.35 (s, 1H). MS (ES+): m/z 403.2 (MH⁺).

Example-2: 3-((6-(2-Ethyl-1-(4H-1,2,4-triazol-4-yl)butyl)benzo[d]thiazol-2-yl)oxy)-2,2-dimethylpropanoic acid Following the procedure above methyl 3-((6-(2-ethyl-1-(4H-1,2,4-triazol-4-yl)butyl)benzo[d]thiazol-2-yl)oxy)-2,2-dimethylpropanoate was converted to 3-((6-(2-ethyl-1-(4H-1,2,4-triazol-4-yl)butyl)benzo[d]thiazol-2-yl)oxy)-2,2-dimethylpropanoic acid. ¹H NMR (CDCl₃, 300 MHz): δ 0.76-0.89 (m, 6H), 1.10-1.40 (m 10H), 2.36-2.46 (m, 1H), 4.61 (s, 2H), 5.21 (d, J=11.4 Hz, 1H), 7.38 (dd, J=8.4, 2.1 Hz, 1H), 7.61 (d, J=8.1 Hz, 1H), 7.72 (d, J=1.5 Hz, 1H), 8.53 (s, 2H). MS (ES+): m/z 403.2 (MH⁺).

Example-3: 1-(((6-(2-Ethyl-1-(1H-1,2,4-triazol-1-yl)butyl)benzo[d]thiazol-2-yl)oxy)methyl)cyclopentanecarboxylic acid Step-1: Ethyl 1-(((6-(2-ethylbutanoyl)benzo[d]thiazol-2-yl)oxy)methyl)cyclopentanecarboxylate To a mixture of 1-(2-bromobenzo[d]thiazol-6-yl)-2-ethylbutan-1-one (5 g, 16.02 mmol) and ethyl 1-(hydroxymethyl)cyclopentanecarboxylate (3.31 g, 19.22 mmol) in THF (100 mL) at −10° C. was added sodium hydride (60%, 769 mg, 19.22 mmol) and the mixture was stirred for 15 min at −10° C. The reaction was allowed to warm to RT and stirred at RT for 2 h. Water was added and THF was removed at reduced pressure. Water was added and extracted with ethyl acetate. The combined organic layers were dried over anhydrous sodium sulfate and evaporated under reduced pressure. The crude product was purified by silica gel column chromatography eluting with 0→10% ethyl acetate in hexanes to afford ethyl 1-(((6-(2-ethylbutanoyl)benzo[d]thiazol-2-yl)oxy)methyl)cyclopentanecarboxylate. ¹H NMR (CDCl₃, 300 MHz): δ 0.88 (t, J=7.5 Hz, 6H), 1.22 (t, J=7.2 Hz, 3H), 1.51-1.87 (m, 10H), 2.10-2.22 (m, 2H), 3.26-3.36 (m, 1H), 4.17 (q, J=6.9 Hz, 2H), 4.69 (s, 2H), 7.71 (dd, J=8.4, 0.3 Hz, 1H), 7.98 (dd, J=6.9, 1.5 Hz, 1H), 8.29 (d, J=1.2 Hz, 1H).

Step-2: Ethyl 1-(((6-(2-ethyl-1-hydroxybutyl)benzo[d]thiazol-2-yl)oxy)methyl)cyclopentanecarboxylate To a solution of ethyl 1-(((6-(2-ethylbutanoyl)benzo[d]thiazol-2-yl)oxy)methyl)cyclopentanecarboxylate (4.04 g, 10.02 mmol) in ethanol (80 mL) at RT was added sodium borohydride (758 mg, 20.04 mmol) and the mixture was stirred overnight. Water was added and the reaction mixture was evaporated under reduced pressure. The residue was dissolved in water and extracted with ethyl acetate. The combined organic layers were dried over anhydrous sodium sulfate and evaporated under reduced pressure to afford ethyl 1-(((6-(2-ethyl-1-hydroxybutyl)benzo[d]thiazol-2-yl)

oxy)methyl)cyclopentanecarboxylate. $^1$H NMR (CDCl$_3$, 300 MHz): δ 8.0-0.92 (m, 6H), 1.10-1.31 (m, 4H), 1.40-1.60 (m, 3H), 1.64-1.82 (m, 5H), 2.10-2.21 (m, 1H), 4.16 (dq, J=7.8, 0.6 Hz, 2H), 4.64 (s, 2H), 4.67-4.72 (m, 1H), 7.29 (d, J=9.0 Hz, 1H), 7.60-7.65 (m, 2H).

Step-3: Ethyl 1-(((6-(2-ethyl-1-(1H-1,2,4-triazol-1-yl)butyl)benzo[d]thiazol-2-yl)oxy)methyl)cyclopentanecarboxylate and ethyl 1-(((6-(2-ethyl-1-(4H-1,2,4-triazol-4-yl)butyl)benzo[d]thiazol-2-yl)oxy)methyl)cyclopentanecarboxylate A mixture of ethyl 1-(((6-(2-ethyl-1-hydroxybutyl)benzo[d]thiazol-2-yl)oxy)methyl)cyclopentanecarboxylate (4.07 g, 10.05 mmol) and carbonylditriazole (4.947 g, 30.14 mmol) in acetonitrile (80 mL) was heated to 75° C. and stirred for 24 h. Water was added and the reaction mixture was evaporated under reduced pressure. To the residue was added water and extracted with dichloromethane. The combined organic layers were dried over anhydrous sodium sulfate and evaporated under reduced pressure. The crude product was purified by silica gel column chromatography eluting with 0→3% methanol in hexanes to afford ethyl 1-(((6-(2-ethyl-1-(1H-1,2,4-triazol-1-yl)butyl)benzo[d]thiazol-2-yl)oxy)methyl)cyclopentanecarboxylate. $^1$H NMR (CDCl$_3$, 300 MHz): δ 0.74-0.85 (m, 6H), 1.08-1.34 (m, 5H), 1.65-1.77 (m, 5H), 2.06-2.20 (m, 2H), 2.45-2.58 (m, 1H), 4.14 (q, J=6.9 Hz, 2H), 4.62 (s, 2H), 5.12 (d, J=10.8 Hz, 1H), 7.42 (dd, J=6.6, 1.8 Hz, 1H), 7.61 (d, J=8.4 Hz, 1H), 7.76 (d, J=1.8 Hz, 1H), 7.93 (s, 1H), 8.11 (s, 1H). Continued elution of the column afforded ethyl 1-(((6-(2-ethyl-1-(4H-1,2,4-triazol-4-yl)butyl)benzo[d]thiazol-2-yl)oxy)methyl)cyclopentanecarboxylate. $^1$H NMR (CDCl$_3$, 300 MHz): δ 0.79-0.89 (m, 6H), 1.08-1.44 (m, 5H), 1.62-1.82 (m, 5H), 2.06-2.21 (m, 2H), 2.22-2.38 (m, 1H), 4.14 (q, J=7.2 Hz, 2H), 4.63 (s, 2H), 5.06 (d, J=10.2 Hz, 1H), 7.26 (dd, J=8.4, 2.1 Hz, 1H), 7.53 (d, J=1.8 Hz, 1H), 7.63 (d, J=8.4 Hz, 1H), 7.94 (s, 1H), 8.24 (s, 2H).

Step-4: 1-(((6-(2-Ethyl-1-(1H-1,2,4-triazol-1-yl)butyl)benzo[d]thiazol-2-yl)oxy)methyl)cyclopentanecarboxylic acid A mixture of ethyl 1-(((6-(2-ethyl-1-(1H-1,2,4-triazol-1-yl)butyl)benzo[d]thiazol-2-yl)oxy)methyl)cyclopentanecarboxylate (1.5 g, 3.29 mmol), lithium hydroxide (690 mg, 16.43 mmol) and water (15 mL) in dioxane (30 mL) was stirred at 50° C. overnight. The reaction was concentrated, water was added and neutralized to pH 6.5-7 and the white precipitate formed was filtered, washed with water and dried. Purification of the crude product by silica gel column chromatography eluting with 0→10% methanol in hexanes to afforded 1-(((6-(2-ethyl-1-(1H-1,2,4-triazol-1-yl)butyl)benzo[d]thiazol-2-yl)oxy)methyl)cyclopentanecarboxylic acid. $^1$H NMR (CDCl$_3$, 300 MHz): δ 0.70-0.86 (m, 6H), 1.08-1.40 (m, 4H), 1.62-1.80 (m, 6H), 2.06-2.21 (m, 2H), 2.45-2.60 (m, 1H), 4.57 (s, 2H), 5.18 (d, J=11.1 Hz, 1H), 7.44 (dd, J=8.1, 1.5 Hz, 1H), 7.58 (d, J=8.1 Hz, 1H), 7.70 (d, J=1.8 Hz, 1H), 7.91 (s, 1H), 8.31 (s, 1H). MS (ES+): m/z 429.2 (MH$^+$).

Example-4: 1-(((6-(2-Ethyl-1-(4H-1,2,4-triazol-4-yl)butyl)benzo[d]thiazol-2-yl)oxy)methyl)cyclopentanecarboxylic acid Following the procedure above ethyl 1-(((6-(2-ethyl-1-(4H-1,2,4-triazol-4-yl)butyl)benzo[d]thiazol-2-yl)oxy)methyl)cyclopentanecarboxylate was converted to 1-(((6-(2-ethyl-1-(4H-1,2,4-triazol-4-yl)butyl)benzo[d]thiazol-2-yl)oxy)methyl)cyclopentanecarboxylic acid. $^1$H NMR (CDCl$_3$, 300 MHz): δ 0.79-0.89 (m, 6H), 1.08-1.40 (m, 4H), 1.62-1.80 (m, 6H), 2.06-2.21 (m, 2H), 2.35-2.45 (m, 1H), 4.52 (s, 2H), 5.18 (d, J=11.1 Hz, 1H), 7.37 (dd, J=8.7, 2.1 Hz, 1H), 7.63 (d, J=8.4 Hz, 1H), 7.70 (d, J=1.8 Hz, 1H), 8.48 (s, 2H). MS (ES+): m/z 429.2 (MH$^+$).

Example-5: 1-(((6-(2-ethyl-1-(1H-1,2,4-triazol-1-yl)butyl)benzo[d]thiazol-2-yl)oxy)methyl)cyclohexanecarboxylic acid Step-1: Ethyl 1-(((6-(2-ethylbutanoyl)benzo[d]thiazol-2-yl)oxy)methyl)cyclohexanecarboxylate To a mixture of 1-(2-bromobenzo[d]thiazol-6-yl)-2-ethylbutan-1-one (5 g, 16.01 mmol) and ethyl 1-(hydroxymethyl)cyclohexanecarboxylate (3.579 g, 19.21 mmol) in THF (100 mL) at −10° C. was added sodium hydride (60%, 769 mg, 19.21 mmol) and the mixture was stirred for 15 min at −10° C. The reaction was allowed to warm to RT and stirred at RT for 2 h. Water was added and THF was removed at reduced pressure. Water was added and extracted with ethyl acetate. The combined organic layers were dried over anhydrous sodium sulfate and evaporated under reduced pressure. The crude product was purified by silica gel column chromatography eluting with 0→10% ethyl acetate in hexanes to afford ethyl 1-(((6-(2-ethylbutanoyl)benzo[d]thiazol-2-yl)oxy)methyl)cyclohexanecarboxylate. $^1$H NMR (CDCl$_3$, 300 MHz): δ 0.88 (t, J=7.5 Hz, 6H), 1.22 (t, J=6.9 Hz, 3H), 1.22-1.70 (m, 10H), 1.70-1.90 (m, 2H), 2.08-2.18 (m, 2H), 3.28-3.38 (m, 1H), 4.17 (q, J=7.2 Hz, 2H), 4.65 (s, 2H), 7.70 (dd, J=8.4, 0.6 Hz, 1H), 7.98 (dd, J=8.7, 1.8 Hz, 1H), 8.28 d (J=1.2 Hz, 1H).

Step-2: Ethyl 1-(((6-(2-ethyl-1-hydroxybutyl)benzo[d]thiazol-2-yl)oxy)methyl)cyclohexanecarboxylate To a solution of ethyl 1-(((6-(2-ethylbutanoyl)benzo[d]thiazol-2-yl)oxy)methyl)cyclohexanecarboxylate (4.04 g, 10.02 mmol) in ethanol (80 mL) at RT was added sodium borohydride (758 mg, 20.04 mmol) and the mixture was stirred overnight. Water was added and the reaction mixture was evaporated under reduced pressure. The residue was dissolved in water and extracted with ethyl acetate. The combined organic layers were dried over anhydrous sodium sulfate and evaporated under reduced pressure to afford ethyl 1-(((6-(2-ethyl-1-hydroxybutyl)benzo[d]thiazol-2-yl)oxy)methyl)cyclohexanecarboxylate. MS (ES+): m/z 420.2 (MH$^+$).

Step-3: Ethyl 1-(((6-(2-ethyl-1-(1H-1,2,4-triazol-1-yl)butyl)benzo[d]thiazol-2-yl)oxy)methyl)cyclohexanecarboxylate and ethyl 1-(((6-(2-ethyl-1-(4H-1,2,4-triazol-4-yl)butyl)benzo[d]thiazol-2-yl)oxy)methyl)cyclohexanecarboxylate A mixture of ethyl 1-(((6-(2-ethyl-1-hydroxybutyl)benzo[d]thiazol-2-yl)oxy)methyl)cyclohexanecarboxylate (4.07 g, 10.05 mmol) and carbonylditriazole (4.947 g, 30.14 mmol) in acetonitrile (80 mL) was heated to 75° C. and stirred for 24 h. Water was added and the reaction mixture was evaporated under reduced pressure. To the residue was added water and extracted with dichloromethane. The combined organic layers were dried over anhydrous sodium sulfate and evaporated under reduced pressure. The crude product was purified by silica gel column chromatography eluting with 0→3% methanol in hexanes to afford ethyl 1-(((6-(2-ethyl-1-(1H-1,2,4-triazol-1-yl)butyl)benzo[d]thiazol-2-yl)oxy)methyl)cyclohexanecarboxylate. $^1$H NMR (CDCl$_3$, 300 MHz): δ 0.78 (t, J=7.5 Hz, 3H), 0.81 (t, J=7.5 Hz, 3H), 1.19 (t, J=6.9 Hz, 3H), 1.06-1.38 (m, 5H), 1.38-1.66 (m, 7H), 2.04-2.18 (m, 2H), 2.44-2.58 (m, 1H), 4.14 (q, J=6.9 Hz, 2H), 4.58 (s, 2H), 5.12 (d, J=10.8 Hz, 1H), 7.42 (dd, J=8.4, 2.1 Hz, 1H), 7.76 (d, J=1.8 Hz, 1H), 7.93 (s, 1H), 8.11 (s, 1H) Continued elution of the column afforded ethyl 1-(((6-(2-ethyl-1-(4H-1,2,4-triazol-4-yl)butyl)benzo[d]thiazol-2-yl)oxy)methyl)cyclohexanecarboxylate. $^1$H NMR (CDCl$_3$, 300 MHz): δ 0.80 (t, J=7.5 Hz, 3H), 0.85 (t, J=7.5 Hz, 3H), 1.19 (t, J=6.9 Hz, 3H), 1.20-1.68 (m, 12H), 2.04-2.18 (m, 2H), 2.22-2.38 (m, 1H), 4.14 (q, J=6.9 Hz, 2H), 4.58 (s, 2H), 5.06 (d, J=10.5 Hz, 1H), 7.26 (dd, J=8.4, 2.1 Hz, 1H), 7.53 (d, J=2.1 Hz, 1H), 8.24 (s, 2H).

Step-4: 1-(((6-(2-Ethyl-1-(1H-1,2,4-triazol-1-yl)butyl)benzo[d]thiazol-2-yl)oxy)methyl)cyclohexanecarboxylic acid A mixture of ethyl 1-(((6-(2-ethyl-1-(1H-1,2,4-triazol-1-yl)butyl)benzo[d]thiazol-2-yl)oxy)methyl)cyclohexanecarboxylate (1.5 g, 3.29 mmol), lithium hydroxide (690 mg, 16.43 mmol) and water (15 mL) in dioxane (30 mL) was stirred at 50° C. overnight. The reaction was concentrated, water was added and neutralized to pH 6.5-7 and the white precipitate formed was filtered, washed with water and dried. Purification of the crude product by silica gel column chromatography eluting with 0→10% methanol in hexanes to afforded 1-(((6-(2-ethyl-1-(1H-1,2,4-triazol-1-yl)butyl)benzo[d]thiazol-2-yl)oxy)methyl)cyclohexanecarboxylic acid. $^1$H NMR (CDCl$_3$, 300 MHz): δ 0.76 (t, J=7.5 Hz, 3H), 0.82 (t, J=7.5 Hz, 3H), 0.92-1.42 (m, 10H), 1.66-1.86 (m, 2H), 2.22-2.72 (m, 3H), 4.37 (s, 2H), 5.08 (d, J=10.8 Hz, 1H), 7.28 (d, J=8.4, Hz, 1H), 7.46 (d, J=8.4 Hz, 1H), 7.67 (s, 1H), 7.96 (s, 1H), 8.17 (s, 1H). MS (ES+): m/z 443.2 (MH$^+$).

Example-6: 1-(((6-(2-Ethyl-1-(4H-1,2,4-triazol-4-yl)butyl)benzo[d]thiazol-2-yl)oxy)methyl)cyclohexanecarboxylic acid Following the procedure above ethyl 1-(((6-(2-ethyl-1-(4H-1,2,4-triazol-4-yl)butyl)benzo[d]thiazol-2-yl)oxy)methyl)cyclohexanecarboxylate was converted to 1-(((6-(2-ethyl-1-(4H-1,2,4-triazol-4-yl)butyl)benzo[d]thiazol-2-yl)oxy)methyl)cyclohexanecarboxylic acid. $^1$H NMR (CDCl$_3$, 300 MHz): δ 0.75 (t, J=6.9 Hz, 3H), 0.82 (t, J=6.9 Hz, 3H), 0.92-1.42 (m, 10H), 1.66-1.86 (m, 2H), 2.18-2.40 (m, 3H), 4.40 (s, 2H), 5.12 (d, J=10.2 Hz, 1H), 7.0-7.15 (br, 1H), 7.30-7.48 (br, 1H), 8.15 (s, 1H), 8.37 (s, 2H). MS (ES+): m/z 443.2 (MH$^+$).

Example-7: 4-(6-(2-ethyl-1-(1H-1,2,4-triazol-1-yl)butyl)benzo[d]thiazol-2-yl)benzoic acid

Step-1: 1-(2-Bromobenzo[d]thiazol-6-yl)-2-ethylbutan-1-ol

To solution of 1-(2-bromobenzo[d]thiazol-6-yl)-2-ethylbutan-1-one (200 mg, 0.64 mmol) in methanol (7 mL) was added sodium borohydride (50 mg, 1.322 mmol) and the mixture was stirred for 3 h. Water was added and evaporated under reduced pressure. The residue was dissolved in water and extracted with ethyl acetate. The combined organic layers were dried over anhydrous sodium sulfate and evaporated. The crude product was purified by silica gel column chromatography eluting with 0→10% ethyl acetate in hexanes to afford 1-(2-bromobenzo[d]thiazol-6-yl)-2-ethylbutan-1-ol. MS (ES+): m/z 314.2 (M+).

Step-2: Methyl 4-(6-(2-ethyl-1-hydroxybutyl)benzo[d]thiazol-2-yl)benzoate

A mixture of 1-(2-bromobenzo[d]thiazol-6-yl)-2-ethylbutan-1-ol (40 mg, 0.127 mmol), (4-(methoxycarbonyl)phenyl)boronic acid (25.3 mg, 0.14 mmol), tetrakis(triphenylphosphine)palladium (14.7 mg, 0.013 mmol), potassium carbonate (53 mg, 0.381 mmol), DME (2 mL) and water (0.4 mL) was degassed, filled with N$_2$, and heated to 80° C. and stirred overnight. The reaction mixture was evaporated. The crude product was purified by column chromatography using 0→30% ethyl acetate in hexanes to afford methyl 4-(6-(2-ethyl-1-hydroxybutyl)benzo[d]thiazol-2-yl)benzoate. $^1$H NMR (CDCl$_3$, 300 MHz): δ 0.88 (t, J=7.2 Hz, 3H), 0.90 (t, J=7.2 Hz, 3H), 1.18-1.36 (m, 2H), 1.40-1.58 (m, 2H), 1.58-1.70 (m, 1H), 3.95 (s, 3H), 4.79 (d, J=6.3 Hz, 1H), 7.43 (dd, J=8.7, 1.8 Hz, 1H), 7.87 (d, J=1.8 Hz, 1H), 8.01 (d, J=8.4 Hz, 1H), 8.10 (s, 4H).

Step-3: Methyl 4-(6-(2-ethyl-1-(1H-1,2,4-triazol-1-yl)butyl)benzo[d]thiazol-2-yl)benzoate and methyl 4-(6-(2-ethyl-1-(4H-1,2,4-triazol-4-yl)butyl)benzo[d]thiazol-2-yl)benzoate A mixture of methyl 4-(6-(2-ethyl-1-hydroxybutyl)benzo[d]thiazol-2-yl)benzoate (43 mg, 0.116 mmol) and carbonyldi triazole (38.2 mg, 0.233 mmol) in acetonitrile (7 mL) was heated to 75° C. and stirred for 24 h. Water was added and the reaction mixture was evaporated under reduced pressure. To the residue was added water and extracted dichloromethane. The combined organic layers were dried over anhydrous sodium sulfate and evaporated under reduced pressure. The crude product was purified by silica gel column chromatography eluting with 0→5% methanol in hexanes to afford methyl 4-(6-(2-ethyl-1-(1H-1,2,4-triazol-1-yl)butyl)benzo[d]thiazol-2-yl)benzoate $^1$H NMR (CDCl$_3$, 300 MHz): δ 0.79 (t, J=7.2 Hz, 3H), 0.83 (t, J=7.2 Hz, 3H), 1.20-1.40 (m, 4H), 2.55-2.68 (m, 1H), 3.92 (s, 3H), 5.34 (d, J=11.1 Hz, 1H), 7.67 (dd, J=8.7, 1.8 Hz, 1H), 7.93 (s, 1H), 8.01 (d, J=8.7 Hz, 1H), 8.05-8.18 (m, 5H), 8.39 (s, 1H). Continued elution of the column afforded methyl 4-(6-(2-ethyl-1-(4H-1,2,4-triazol-4-yl)butyl)benzo[d]thiazol-2-yl)benzoate. $^1$H NMR (CDCl$_3$, 300 MHz): δ 0.81 (t, J=7.5 Hz, 3H), 0.86 (t, J=7.5 Hz, 3H), 1.20-1.44 (m, 4H), 2.40-2.55 (m, 1H), 3.92 (s, 3H), 5.30 (d, J=11.1 Hz, 1H), 7.55 (dd, J=8.4, 1.8 Hz, 1H), 8.01 (d, J=1.5 Hz, 1H), 8.03 (d, J=8.4 Hz, 1H), 8.08 (s, 4H), 8.53 (s, 2H)

Step-4: 4-(6-(2-Ethyl-1-(1H-1,2,4-triazol-1-yl)butyl)benzo[d]thiazol-2-yl)benzoic acid A mixture of methyl 4-(6-(2-ethyl-1-(1H-1,2,4-triazol-1-yl)butyl)benzo[d]thiazol-2-yl)benzoate (15 mg, 0.036 mmol), lithium hydroxide (7.5 mg, 0.18 mmol) and water (0.5 mL) in dioxane (1 mL) was stirred at 50° C. overnight. The reaction was concentrated, water was added and neutralized to pH 6.5-7 and evaporated. The residue was dissolved in 5% methanol in dichloromethane, filtered and evaporated under reduced pressure. The crude product was purified by silica gel column chromatography eluting with 0→10% methanol in hexanes to afford 4-(6-(2-ethyl-1-(1H-1,2,4-triazol-1-yl)butyl)benzo[d]thiazol-2-yl)benzoic acid.

¹H NMR (CDCl₃, 300 MHz): δ 0.78 (t, J=7.2 Hz, 3H), 0.83 (t, J=7.2 Hz, 3H), 1.10-1.40 (m, 4H), 2.50-2.66 (m, 1H), 5.33 (d, J=11.4 Hz, 1H), 7.62 (dd, J=8.7, 1.5 Hz, 1H), 7.90-8.04 (m, 4H), 8.04-8.14 (m, 3H), 8.41 (s, 1H). MS (ES+): m/z 407.2 (MH⁺).

Example-8: 4-(6-(2-ethyl-1-(4H-1,2,4-triazol-4-yl)butyl)benzo[d]thiazol-2-yl)benzoic acid Following the procedure above methyl 4-(6-(2-ethyl-1-(4H-1,2,4-triazol-4-yl)butyl)benzo[d]thiazol-2-yl)benzoate was converted to 4-(6-(2-ethyl-1-(4H-1,2,4-triazol-4-yl)butyl)benzo[d]thiazol-2-yl)benzoic acid. ¹H NMR (CDCl₃, 300 MHz): δ 0.79 (t, J=7.8 Hz, 3H), 0.86 (t, J=7.2 Hz, 3H), 1.10-1.44 (m, 4H), 2.34-2.48 (m, 1H), 5.22 (d, J=11.1 Hz, 1H), 7.41 (d, J=8.7, 1H), 7.86-8.00 (m, 4H), 8.04-8.14 (m, 2H), 8.46 (s, 2H). MS (ES+): m/z 407.2 (MH⁺).

Using the aforementioned methods, the following additional compounds can be made: 2-chloro-4-(6-(2-ethyl-1-(1H-1,2,4-triazol-1-yl)butyl)benzo[d]thiazol-2-yl)benzoic acid, 2-chloro-4-(6-(2-ethyl-1-(4H-1,2,4-triazol-4-yl)butyl)benzo[d]thiazol-2-yl)benzoic acid, 4-(6-(2-ethyl-1-(1H-1,2,4-triazol-1-yl)butyl)benzo[d]thiazol-2-yl)-2-(trifluoromethyl)benzoic acid, 4-(6-(2-ethyl-1-(1H-1,2,4-triazol-1-yl)butyl)benzo[d]thiazol-2-yl)-2-fluorobenzoic acid, 4-(6-(2-ethyl-1-(4H-1,2,4-triazol-4-yl)butyl)benzo[d]thiazol-2-yl)-2-(trifluoromethyl)benzoic acid, 4-(6-(2-ethyl-1-(4H-1,2,4-triazol-4-yl)butyl)benzo[d]thiazol-2-yl)-2-fluorobenzoic acid, 1-(((6-(2-ethyl-1-(1H-1,2,4-triazol-1-yl)butyl)benzo[d]thiazol-2-yl)oxy)methyl)cyclobutanecarboxylic acid, 1-(((6-(2-ethyl-1-(1H-1,2,4-triazol-1-yl)butyl)benzo[d]thiazol-2-yl)oxy)methyl)cycloheptanecarboxylic acid, 1-(((6-(2-ethyl-1-(1H-1,2,4-triazol-1-yl)butyl)benzo[d]thiazol-2-yl)oxy)methyl)cyclopropanecarboxylic acid, 1-(((6-(2-ethyl-1-(4H-1,2,4-triazol-4-yl)butyl)benzo[d]thiazol-2-yl)oxy)methyl)cyclobutanecarboxylic acid, 1-(((6-(2-ethyl-1-(4H-1,2,4-triazol-4-yl)butyl)benzo[d]thiazol-2-yl)oxy)methyl)cycloheptanecarboxylic acid, 1-(((6-(2-ethyl-1-(4H-1,2,4-triazol-4-yl)butyl)benzo[d]thiazol-2-yl)oxy)methyl)cyclopropanecarboxylic acid, 2-ethyl-2-(((6-(2-ethyl-1-(1H-1,2,4-triazol-1-yl)butyl)benzo[d]thiazol-2-yl)oxy)methyl)butanoic acid, and 2-ethyl-2-(((6-(2-ethyl-1-(4H-1,2,4-triazol-4-yl)butyl)benzo[d]thiazol-2-yl)oxy)methyl)butanoic acid.

Example 9: Biological Activity In Vitro

CYP26 Inhibition.

Compounds of formula (I) were tested for activity in a substrate depletion assay for ATRA metabolism in mouse microsomes. Mouse microsomes were produced by Xenotech from the livers of mice treated with ATRA for four days to induce CYP26. ATRA metabolism in these microsomes was tested at a final concentration of 0.1 mg protein/mL in a 100 mM phosphate buffer (pH 7.4) containing an NADPH regenerating system (BD Biosciences catalog #451200 and 451220). The assay was run in a 100 µL reaction volume and stopped with an equal volume of methanol. ATRA concentrations at the beginning and end of incubations were determined using HPLC and LC-MS/MS. The "induced" mouse microsomes have vastly increased CYP26 transcription and ATRA metabolic activity compared to normal microsomes (~100 fold) and ATRA metabolic activity displays classical Michaelis-Menten kinetics with a Km of ~4 nM, which is similar to the Km reported for the human recombinant enzyme (~10 nM). At a starting ATRA concentration of approximately 10 nM and under conditions of significant substrate turnover, inventive compound completely inhibits ATRA metabolism with an IC$_{50}$ of 2 nM. Other compounds of formula (I) are similarly potent, for example with an IC$_{50}$ of 1.6 nM. Most of the inventive compounds showed IC50 of <1.0 uM.

The following compounds of Formula (I) inhibited CYP26 with an IC$_{50}$ of <1.0 µM:
1-(((6-(2-ethyl-1-(1H-1,2,4-triazol-1-yl)butyl)benzo[d]thiazol-2-yl)oxy)methyl)cyclohexanecarboxylic acid; 1-(((6-(2-ethyl-1-(1H-1,2,4-triazol-1-yl)butyl)benzo[d]thiazol-2-yl)oxy)methyl)cyclopentanecarboxylic acid; 1-(((6-(2-ethyl-1-(4H-1,2,4-triazol-4-yl)butyl)benzo[d]thiazol-2-yl)oxy)methyl)cyclohexanecarboxylic acid; 1-(((6-(2-ethyl-1-(4H-1,2,4-triazol-4-yl)butyl)benzo[d]thiazol-2-yl)oxy)methyl)cyclopentanecarboxylic acid; 3-((6-(2-ethyl-1-(1H-1,2,4-triazol-1-yl)butyl)benzo[d]thiazol-2-yl)oxy)-2,2-dimethylpropanoic acid; 3-((6-(2-ethyl-1-(4H-1,2,4-triazol-4-yl)butyl)benzo[d]thiazol-2-yl)oxy)-2,2-dimethylpropanoic acid; 4-(6-(2-ethyl-1-(1H-1,2,4-triazol-1-yl)butyl)benzo[d]thiazol-2-yl)benzoic acid; 4-(6-(2-ethyl-1-(4H-1,2,4-triazol-4-yl)butyl)benzo[d]thiazol-2-yl)benzoic acid.

Selectivity for other P450 enzymes. To assess the selectivity of compounds embodied herein, activity was evaluated against CYP3A4, the cytochrome P450 enzyme responsible for metabolism of many drugs and whose inhibition may thus cause drug-drug interactions. Commercially available recombinant enzymes and assay kits were used for this test. Compounds were demonstrated to have selectivity against CYP3A4. Other CYP enzymes that were evaluated included CYP1A2, CYP2B6, CYP2C8, CYP2C9, CYP2C19, CYP2D6, CYP17 and CYP19. All compounds inhibited CYP26 at least two fold better than at least one of the other CYP enzymes; i.e., the IC$_{50}$ for inhibition of CYP26 was at least half that for one or more other CYP enzymes.

What is claimed is:

1. A compound selected from the group consisting of: 4-(6-(2-ethyl-1-(1H-1,2,4-triazol-1-yl)butyl)benzo[d]thiazol-2-yl)benzoic acid; 4-(6-(2-ethyl-1-(4H-1,2,4-triazol-4-yl)butyl)benzo[d]thiazol-2-yl)benzoic acid; 2-chloro-4-(6-(2-ethyl-1-(1H-1,2,4-triazol-1-yl)butyl)benzo[d]thiazol-2-yl)benzoic acid, 2-chloro-4-(6-(2-ethyl-1-(4H-1,2,4-triazol-4-yl)butyl)benzo[d]thiazol-2-yl)benzoic acid, 4-(6-(2-ethyl-1-(1H-1,2,4-triazol-1-yl)butyl)benzo[d]thiazol-2-yl)-2-(trifluoromethyl)benzoic acid, 4-(6-(2-ethyl-1-(1H-1,2,4-triazol-1-yl)butyl)benzo[d]thiazol-2-yl)-2-fluorobenzoic acid, 4-(6-(2-ethyl-1-(4H-1,2,4-triazol-4-yl)butyl)benzo[d]thiazol-2-yl)-2-(trifluoromethyl)benzoic acid, and 4-(6-(2-ethyl-1-(4H-1,2,4-triazol-4-yl)butyl)benzo[d]thiazol-2-yl)-2-fluorobenzoic acid.

2. A pharmaceutical composition comprising a compound of claim 1 and a pharmaceutically acceptable carrier, excipient or diluent.

3. A method of treatment or lessening of the severity of a condition or disease associated with modulation of ATRA levels comprising administering to a subject in need thereof a compound of claim 1 or a pharmaceutical composition thereof.

4. The method of claim 3 wherein the condition or disease is associated with or characterized as cancer, emphysema, atherosclerosis, or a neurological disorder.

5. The method of claim 3 wherein the condition or disease is associated with or characterized by increased, excessive or inappropriate fibrosis.

6. The method of claim 5 wherein the disease or condition is fibrotic liver disease, hepatic ischemia-reperfusion injury, cerebral infarction, ischemic heart disease, renal disease or lung (pulmonary) fibrosis.

7. The method of claim 5 wherein the disease or condition is liver fibrosis associated with hepatitis C, hepatitis B, delta hepatitis, chronic alcoholism, non-alcoholic steatohepatitis, extrahepatic obstructions, cholangiopathies, autoimmune liver disease, and inherited metabolic disorders; damaged and/or ischemic organs, transplants or grafts; ischemia/reperfusion injury; stroke; cerebrovascular disease; myocardial ischemia; renal failure; renal fibrosis or idiopathic pulmonary fibrosis.

8. The method of claim 5 wherein the disease or condition is treatment of wounds for acceleration of healing; vascularization of a damaged and/or ischemic organ, transplant or graft; amelioration of ischemia/reperfusion injury in the brain, heart, liver, kidney, and other tissues and organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease; lung fibrosis; radiocontrast nephropathy; fibrosis secondary to renal obstruction; renal trauma and transplantation; renal failure secondary to chronic diabetes and/or hypertension; amyotrophic lateral sclerosis, muscular dystrophy, scleroderma, chronic obstructive pulmonary disease, diabetes mellitus, multiple sclerosis, trauma to the central nervous system, Parkinson's disease, Alzheimer's disease, and a hereditary neurodegenerative disorder.

9. The method of claim 3 wherein the disease is a skin disease.

10. The method of claim 3 wherein the condition or disease is associated with emphysema.

11. The method of claim 3 wherein the condition or disease is associated with or characterized as atherosclerosis.

12. The method of claim 3 wherein the condition or disease is associated with or characterized by increased, excessive or inappropriate cellular proliferation.

13. The method of claim 12 wherein the condition or disease is cancer, psoriasis, an inflammatory joint disease or an inflammatory skin disease.

14. The method of claim 12 wherein the condition or disease is prostate cancer, breast cancer or ovarian cancer.

15. A method for inhibiting CYP26 in a subject comprising administering to said subject a compound of claim 1 or a pharmaceutical composition thereof.

16. The method of claim 5 wherein the disease or condition is stones in the bile duct, primary biliary cirrhosis, sclerosing cholangitis, Wilson's disease, hemochromatosis or alpha-1 antitrypsin deficiency.

17. The method of claim 8 wherein the hepatic disease is fibrosis and cirrhosis.

18. The method of claim 8 wherein the hereditary neurodegenerative disorder is a leukodystrophy.

19. The method of claim 18 wherein the leukodystrophy is metachromatic leukodystrophy, Refsum's disease, adrenoleukodystrophy, Krabbe's disease, phenylketonuria, Canavan disease, Pelizaeus-Merzbacher disease or Alexander's disease.

20. The method of claim 9 wherein the skin disease is selected from among actinic keratoses, arsenic keratoses, inflammatory and non-inflammatory acne, psoriasis, ichthyosis, keratinization and hyperproliferative disorders of the skin, eczema, atopic dermatitis, Darriers disease, lichen planus; for treating and reversal of glucocorticoid, age, and photo damage to the skin or fine lines or wrinkles.

21. The method of claim 20 wherein the ichthyosis is ichthyosis vulgaris, lamellar ichthyosis, X-linked ichthyosis, congenital ichthyosiform erythroderma, epidermolytic hyperkeratosis (bullous ichthyosis), harlequin-type ichthyosis, ichthyosis bullosa of Siemens, ichthyosis hystrix, Curth-Macklin type, hystrix-like ichthyosis with deafness, lamellar ichthyosis, type 1, lamellar ichthyosis, type 2, lamellar ichthyosis, type 3 lamellar ichthyosis, type 4, lamellar ichthyosis, type 5, or autosomal recessive congenital ichthyosis.

* * * * *